United States Patent
Baarman et al.

(10) Patent No.: US 9,597,261 B2
(45) Date of Patent: Mar. 21, 2017

(54) PILL DISPENSER

(71) Applicant: Access Business Group International LLC, Ada, MI (US)

(72) Inventors: David W. Baarman, Fennville, MI (US); Sean T. Eurich, Holland, MI (US); Scott A. Mollema, Rockford, MI (US); Cody D. Dean, Grand Rapids, MI (US); Neil W. Kuyvenhoven, Ada, MI (US); Matthew K. Runyon, Kentwood, MI (US); Joseph C. Van Den Brink, West Olive, MI (US); Ryan D. Schamper, Grand Haven, MI (US)

(73) Assignee: Access Business Group International LLC, Ada, MI (US)

( * ) Notice: Subject to any disclaimer, the term of this patent is extended or adjusted under 35 U.S.C. 154(b) by 0 days.

(21) Appl. No.: 14/940,995

(22) Filed: Nov. 13, 2015

(65) Prior Publication Data

US 2016/0128906 A1    May 12, 2016

Related U.S. Application Data

(63) Continuation of application No. 13/455,634, filed on Apr. 25, 2012, now Pat. No. 9,218,458.

(Continued)

(51) Int. Cl.
*A61J 7/04* (2006.01)
*A61J 7/00* (2006.01)
(Continued)

(52) U.S. Cl.
CPC .............. *A61J 7/04* (2013.01); *A61J 7/0076* (2013.01); *A61J 7/0084* (2013.01); *A61J 7/02* (2013.01);
(Continued)

(58) Field of Classification Search
CPC .......... A61J 7/0481; A61J 7/04; A61J 7/0084; G07F 17/0092
(Continued)

(56) References Cited

U.S. PATENT DOCUMENTS

| 3,998,356 A | 12/1976 | Christensen |
| 4,911,327 A | 3/1990 | Shepherd et al. |

(Continued)

FOREIGN PATENT DOCUMENTS

| EP | 0 924 655 | 6/1999 |
| EP | 1 813 249 | 8/2007 |

(Continued)

OTHER PUBLICATIONS

International Search Report and the Written Opinion of the International Searching Authority for International Application No. PCT/US2012/034943 mailed Oct. 10, 2012.

*Primary Examiner* — Timothy Waggoner
(74) *Attorney, Agent, or Firm* — Warner Norcross & Judd LLP

(57) ABSTRACT

A pill dispensing system that includes pill packages that can be used to dispense pills manually or with a dispenser system to provide enhanced functionality. The packages can be provided with information relating to the packaged pills or to the use of the packaged pills. By reading the information from the package, the dispenser system can know what is in the package, when it is to be taken and can understand and track inventory. The dispenser system provides reminders of when the pills should be taken. The dispenser system may have the ability to key a specific electronic device, such as a cell phone, to a specific user and the dispenser system may require the electronic device to be within proximity of the dispenser system before dispensing pills for that user.

38 Claims, 18 Drawing Sheets

Related U.S. Application Data

(60) Provisional application No. 61/478,915, filed on Apr. 25, 2011.

(51) Int. Cl.
*G06F 19/00* (2011.01)
*A61J 7/02* (2006.01)
*G06Q 10/08* (2012.01)
*G07F 17/00* (2006.01)
*A61J 1/03* (2006.01)

(52) U.S. Cl.
CPC ........ *A61J 7/0481* (2013.01); *G06F 19/3462* (2013.01); *G06Q 10/087* (2013.01); *A61J 1/03* (2013.01); *A61J 2200/30* (2013.01); *A61J 2200/74* (2013.01); *A61J 2205/60* (2013.01); *G07F 17/0092* (2013.01)

(58) Field of Classification Search
USPC ........................................................ 700/237
See application file for complete search history.

(56) References Cited

U.S. PATENT DOCUMENTS

| | | | |
|---|---|---|---|
| 5,522,525 A | 6/1996 | McLaughlin et al. | |
| 6,216,910 B1 | 4/2001 | Numerick | |
| 6,805,259 B2* | 10/2004 | Stevens | B65B 5/103 198/757 |
| 7,080,755 B2* | 7/2006 | Handfield | A61J 7/0084 700/237 |
| 7,269,476 B2* | 9/2007 | Ratnakar | A61J 7/0481 700/236 |
| 7,831,336 B2 | 11/2010 | Gumpert | |
| 7,873,435 B2 | 1/2011 | Yuyama et al. | |
| 2006/0060645 A1 | 3/2006 | Udaka et al. | |
| 2007/0108219 A1 | 5/2007 | Handfeld et al. | |

FOREIGN PATENT DOCUMENTS

| | | |
|---|---|---|
| JP | H06-511183 | 12/1994 |
| JP | H10-201827 | 8/1998 |
| JP | H11-280317 | 10/1999 |
| JP | 2002-165866 | 6/2002 |
| JP | 2004-148036 | 5/2004 |
| JP | 2005-40459 | 2/2005 |
| JP | 2006-092197 | 4/2006 |
| JP | 2010-170504 | 8/2010 |
| WO | 94/04966 | 3/1994 |
| WO | 00/56264 | 9/2000 |
| WO | 01/94205 | 12/2001 |

\* cited by examiner

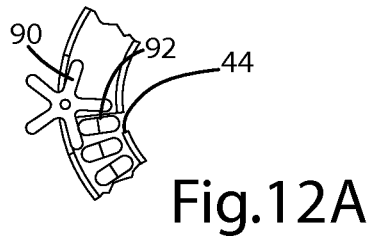
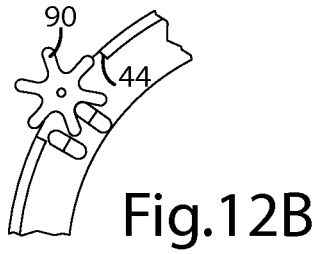
Fig.12A   Fig.12B
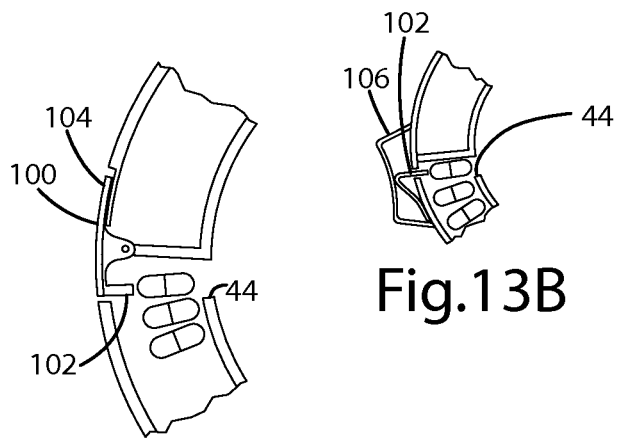
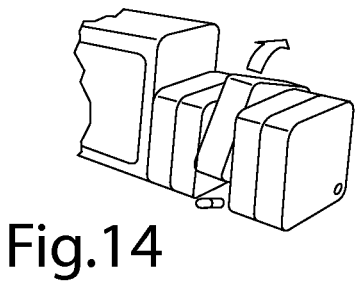
Fig.13B
Fig.13A
Fig.14
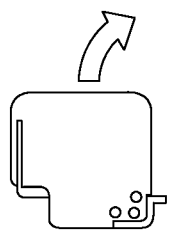
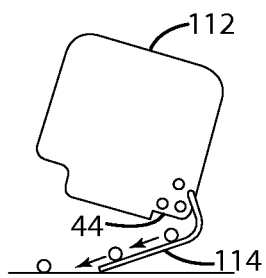
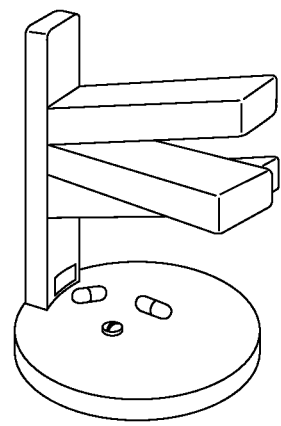
Fig. 15A   Fig. 15B   Fig. 16

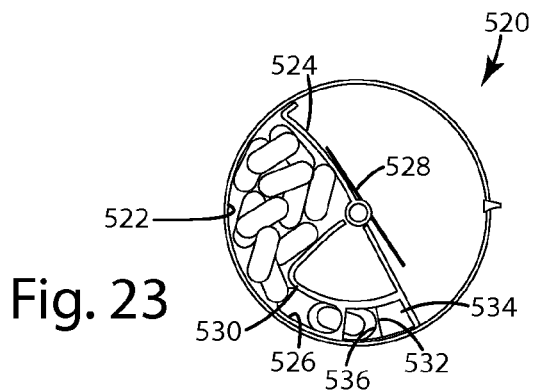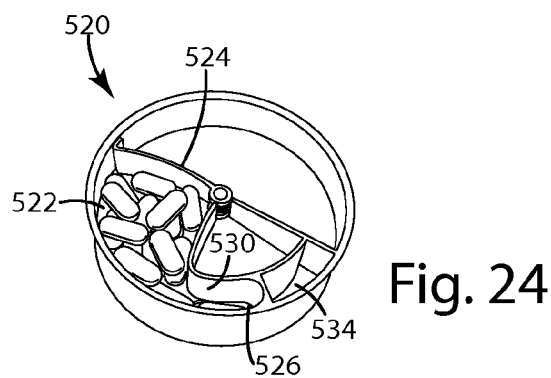
Fig. 23　　　　　　　　　　Fig. 24
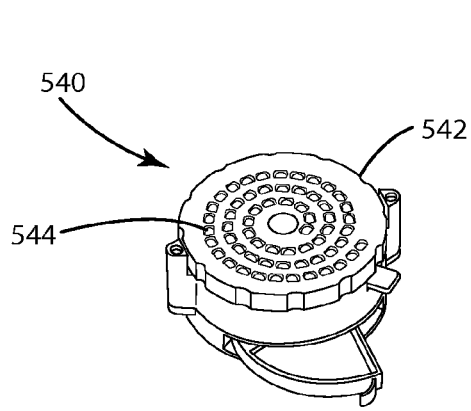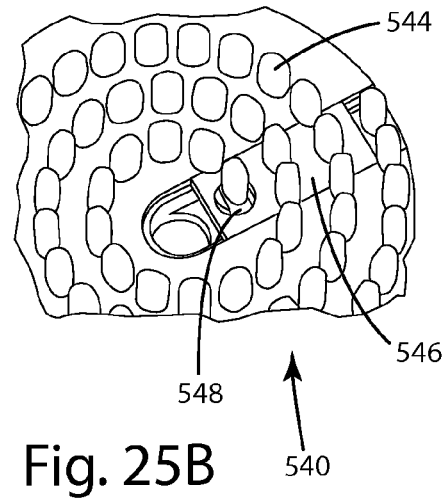
Fig. 25A　　　　　　　　　Fig. 25B
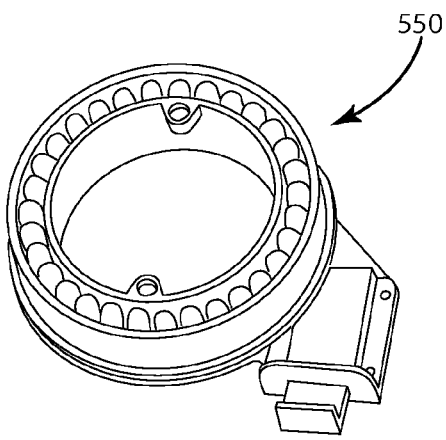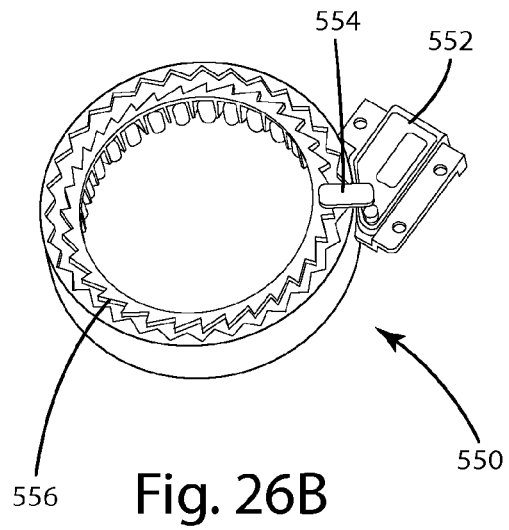
Fig. 26A　　　　　　　　　Fig. 26B

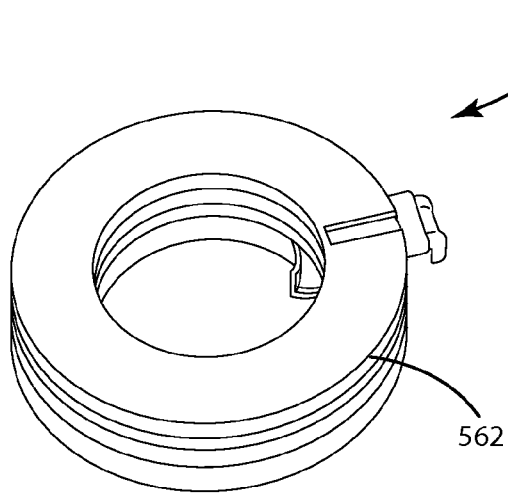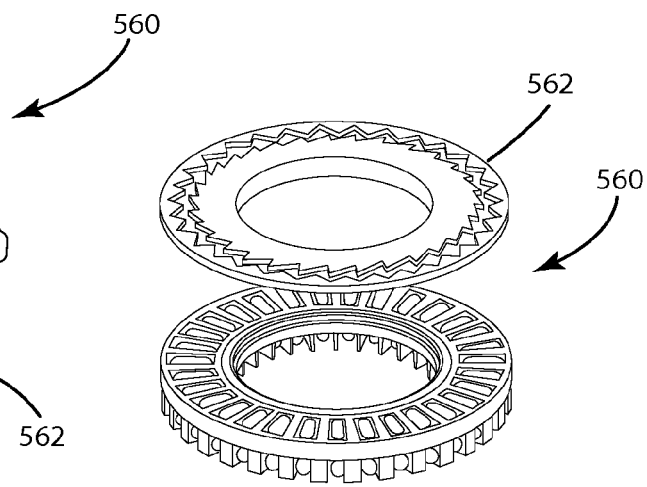
Fig. 27A   Fig. 27B
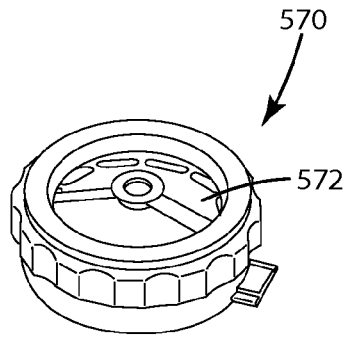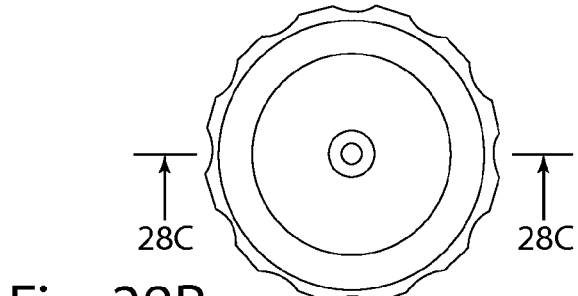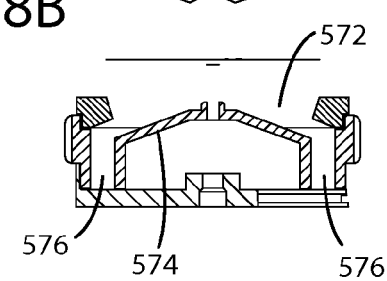
Fig. 28A   Fig. 28B   Fig. 28C
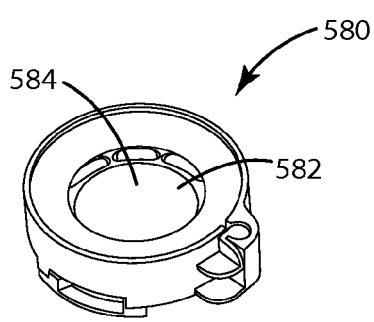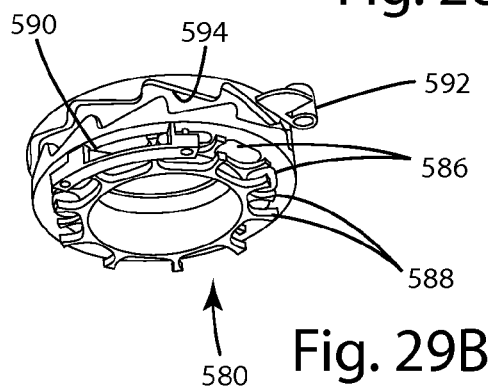
Fig. 29A   Fig. 29B

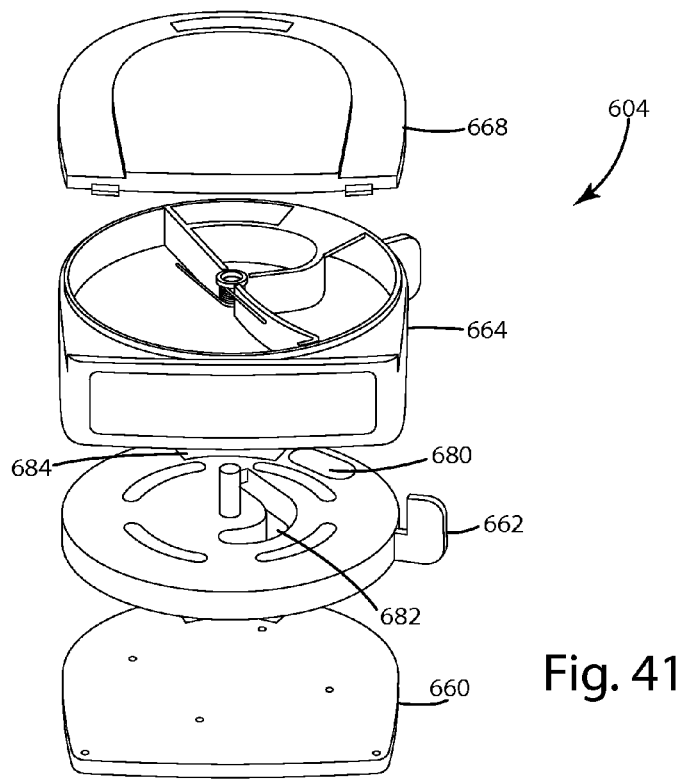
Fig. 41
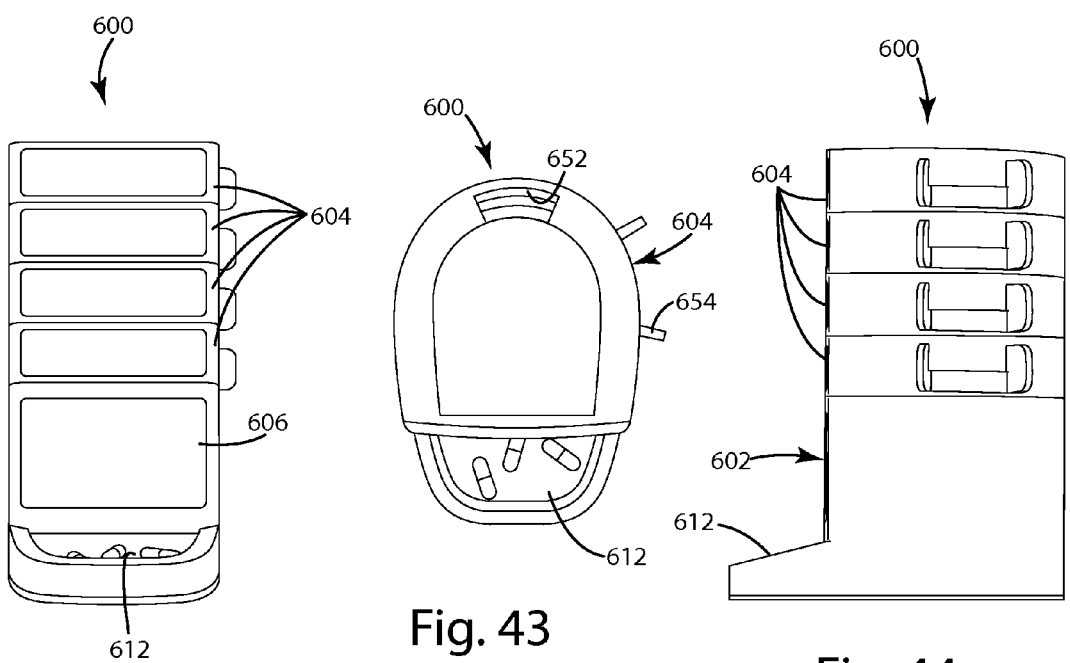
Fig. 42
Fig. 43
Fig. 44

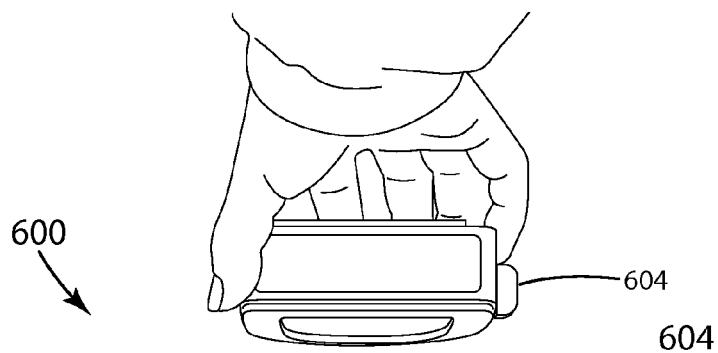
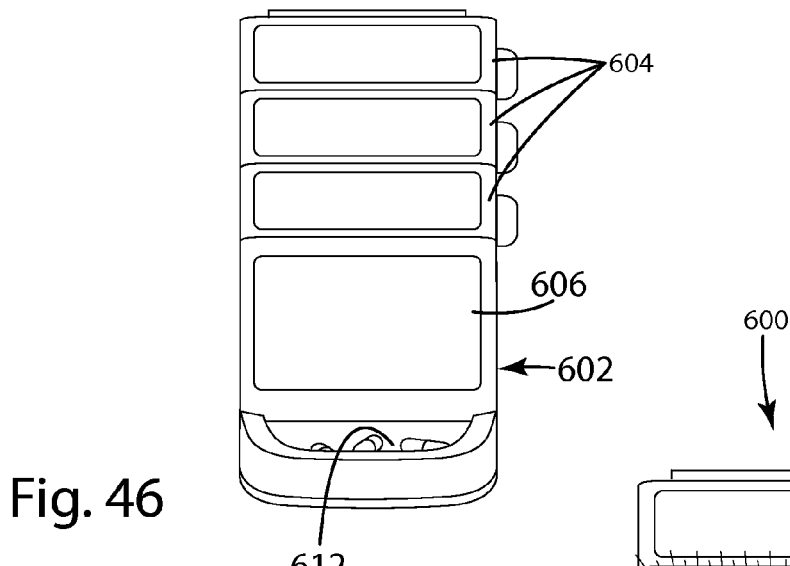
Fig. 46
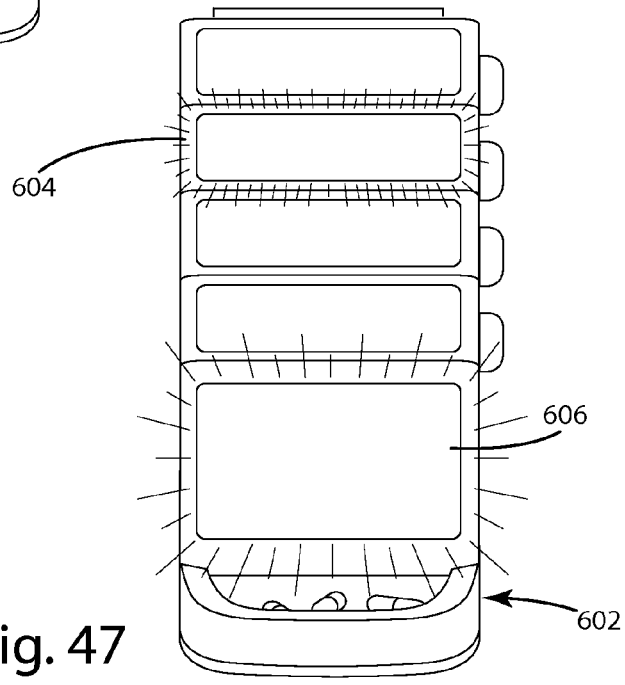
Fig. 47

PILL DISPENSER

FIELD OF THE INVENTION

The present invention relates to pill dispensers and more particularly to a pill dispenser system for dispensing pills and tracking pill dispensing information.

BACKGROUND OF THE INVENTION

Many consumers do not take their prescription drugs or supplements correctly. Overdosing and under dosing can have serious side effects. It can be difficult for doctors and health specialists to monitor patients' use of prescription drugs and supplements. When consumers are unorganized, it can be difficult to find pills and easy to forget to take them. Patients can get confused and take the wrong dosage. Containers can be difficult to open, especially for seniors. Some drugs, when taken along with others, can have serious side effects. Many people believe if a drug is prescribed by a doctor, it is safe. Understanding health and what options you have is getting continuously more complex. This is true in the dispensing of health supplements and in medications. Today we find it difficult to dispense manually and to offer an automated solution. It is typically one or the other. In the past, systems have been difficult to program and dispense, especially when the dose or number can change.

SUMMARY OF THE INVENTION

The present invention provides a pill dispensing system that includes pill packages that can be used to dispense pills manually or with a dispenser system to provide enhanced functionality. In one embodiment, the package is a child safe storage system for pills that can be placed in a dispenser system for dispensing, which may occur manually or with some degree of automation. One or more packages may be placed on a single dispenser system base so that different types of pills can be dispensed from the dispenser system. For example, in one embodiment, one or more packages may be stacked on a dispenser system base.

In one embodiment, the dispenser system may provide some degree of automation to pill dispensing. The package(s) may work in conjunction with the dispenser system base to form a pill dispensing system. The dispenser system base may interact with the packages to provide the desired level of automation. In one embodiment, the packages are provided with information relating to the packaged pills or to the use of the packaged pills. The package can store essentially any information that could be relevant to the pills, use of the pills or the dispensing system, such as pill type, prescribed dosage, consumption frequency, manufacturer, manufacturing date, consumer name, phone numbers, prescription number, dates, consumer addresses, pharmacy and store addresses, number of refills, refill dates, doctor names, product quantity, warnings, laws, side effects, expiration dates, barcodes, and recommendations.

In one embodiment, the dispenser system base is configured to obtain information from the packages using essentially any data transfer methods and apparatus, whether wired or wireless. For example, the dispenser system base may obtain information from the packages using hardwire communication schemes, RFID, Bluetooth, low power RF data transmission or WiFi. In some applications, the packages may include an RFID chip containing the desired information or a controller with memory storing the desired information. In some applications, the packages may wirelessly receive power from the dispenser system base. For example, the dispenser system base may produce a time-varying electromagnetic field and the packages may includes a secondary in which power is induced by the time-varying electromagnetic field. In such systems, the dispensers and packages may exchange communications using communication signals overlaid onto the electromagnetic field transferring power to the packages. For example, in wirelessly powered systems, the packages and dispenser may communication using backscatter modulation.

The dispenser system base may read information from or write information to the packages in realtime as desired. In one embodiment, the dispenser system base may read information from a package when that package is placed on the dispenser system base. In another embodiment, the dispenser system base may periodically poll the packages to periodically obtain information about the installed packages.

In one embodiment, the package is provided with an identification of the product type stored in the package, the number of pills in the package and information about when it is to be taken. By reading the information from the package, the dispenser system knows what is in the package, when it is to be taken and can understand and track inventory.

In one embodiment, the dispenser system provides reminders of when the pills should be taken. In other embodiments, the dispenser system may automate the process of dispensing the appropriate pills at the appropriate time. For example, the dispenser system may operate the packages to dispense the pills at the appropriate time for consumption.

In another embodiment, the dispenser system may track pill dispensing information. For example, the dispenser system may maintain inventory of the pills in the various installed packages. The dispenser system may use this information to provide inventory information, warn of low inventory and/or provide reordering capabilities. The dispenser system is also able to monitor user statistics like when it dispenses pills and how often it dispenses. For some medications with deadly side effects, the package can limit the number of pills taken at once and the time in between the next dose.

In one embodiment, the dispenser system may be connected to a network and may be configured to provide information via the network. For example, in the context of medication, the dispenser system may communicate pill usage information to a doctor, physician, pharmacist or other health specialist and in the context of food supplements, the dispenser system may communication pill usage information to a food supplement representative. The dispenser system may be use inventory information to reorder pills. For example, the dispenser system may warn the user that inventory is getting low and may request authorization from the user to restock the inventory. Upon authorization, the dispenser system may place an order over the network. As another example of a reordering system, the dispenser system may be configured to automatically reorder pills when the inventory is sufficiently depleted. The dispenser system may also be able to communicate information to the user via the network. For example, the dispenser system may provide a user with a reminder via the network when it is time to take a pill. This reminder may be sent in essentially any form of communication, such as a text message or an email sent to a computer or other type of electronic device. The dispenser system may be capable of communicating directly or indirectly with smart phones, personal digital assistants, tablets and/or other hand held electronic devices.

For example, a smart phone may have an application that provides interaction with the dispenser system via Bluetooth, WiFi, NFC or other forms of communications. The dispenser system may be capable of sending a reminder that appears on the screen of the smart phone to remind the user to take a pill. The dispenser system may also be capable of providing usage statics and reordering information to the user via the network.

The package can prevent unprescribed users from taking pills not prescribed to them. In some embodiments, the system may be made child safe (or child resistant) by requiring operation of more than one mechanism to dispense a pill. For example, in one embodiment, buttons on opposite sides of the package must be pressed simultaneously to dispense a pill. As another example, if the dispenser system has the ability to automate pill dispensing, the dispenser system may include a security feature that prevents unauthorized dispensing of pills. For example, the dispenser system may include a password or some form of biometric input required to activate the dispenser, such as a fingerprint reader or voice recognition/voice identification system. As another example, the dispenser system may have the ability to identify a user based on the presence of an electronic device. The dispenser system may have the ability to key a specific electronic device, such as a cell phone, to a specific user and the dispenser system may require the electronic device to be within proximity of the dispenser system before dispensing pills for that user. The dispenser system may determine the proximity of the keyed electronic devise using capabilities associated with Bluetooth, WiFi, Near Field Communications or other wireless methods and apparatus.

In one embodiment, the package is designed to be a light pipe to allow the dispenser to light the package when it is dispensing. A simple label allows the product type to be lighted through a translucent label for consumer interface. This package will allow pharmacists and manufactures load pills into the package faster and more effectively by helping to eliminate quantity errors.

These and other features of the invention will be more fully understood and appreciated by reference to the description of the embodiments and the drawings.

BRIEF DESCRIPTION OF THE DRAWINGS

FIGS. 12A-B are an alternative embodiment of a mechanism for dispensing pills from a package.

FIGS. 13A-B show alternative embodiments of a mechanism for dispensing pills from a package.

FIG. 14 is an alternative embodiment of a mechanism for dispensing pills from a package.

FIGS. 15A-B are an alternative embodiment of a mechanism for dispensing pills from a package.

FIG. 16 is an alternative embodiment of a mechanism for dispensing pills from a package.

FIG. 23 is a top view of the package of FIG. 22 with the cover removed to show the internal mechanisms.

FIG. 24 is a perspective view of the package of FIG. 22 with the cover removed to show the internal mechanisms.

FIG. 25A-B are illustrations of an alternative mechanism design for a package.

FIG. 26A-B are illustrations of an alternative mechanism design for a package.

FIG. 27A-B are illustrations of an alternative mechanism design for a package.

FIG. 28A-C are illustrations of an alternative mechanism design for a package.

FIG. 29A-B are illustrations of an alternative mechanism design for a package.

FIG. 41 is an exploded perspective view of the package of FIG. 36.

FIG. 42 is a front view of the dispenser system of FIG. 31.

FIG. 43 is a top view of the dispenser system of FIG. 31.

FIG. 44 is a side view of the dispenser system of FIG. 31.

FIG. 46 is a front view showing a package being stacked on the dispenser system.

FIG. 47 is a front view showing a reminder to dispense a pill from the "Vitamin C" package.

Figure 1:
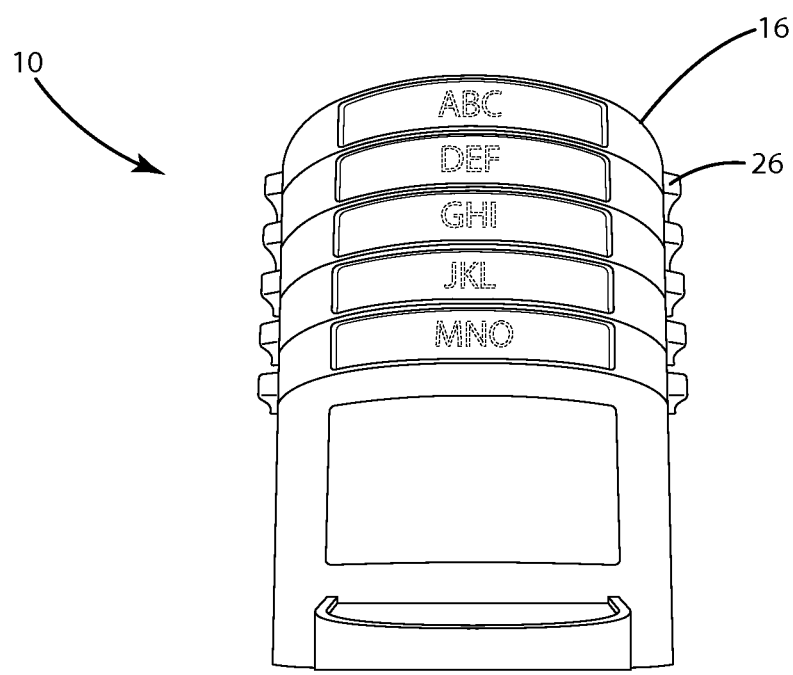
FIG. 1 is a perspective view of a dispenser system in accordance with an embodiment of the present invention.

Before the embodiments of the invention are explained in detail, it is to be understood that the invention is not limited in its application to the details of construction and the arrangement of the components set forth in the following description or illustrated in the drawings. The invention is capable of other embodiments and of being practiced or being carried out in various ways. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof.

DESCRIPTION OF CURRENT EMBODIMENTS

FIGS. 1-5 illustrate one embodiment of a dispenser system, generally designated 10. The illustrated dispenser system 10 includes a dispenser base 14, a plurality of pill bottles or packages 16, and an optional cap 18. Multiple packages 16 can stack on top of one another and be placed on top of the dispenser base 14. A cap 18 can optionally be placed on top of the packages 16 to prevent tampering, to prevent dust from collecting in the system, or for another reason. Each package 16 can include a dispensing element 26 that when actuated dispenses a pill from the package 16 into the outlet tray 12 for consumption.

The dispenser system 14 can include a control system, a display 20, a user interface 20, and a dispenser tray 12. The control system can control the display 20, the user interface 20, the power transmission to the packages, and communication between the dispenser base 14 and the packages 16.

In the illustrated embodiment, the display and the user interface are integrated into a touch screen display 20 that allows a user to interact with the pill dispenser system. The dispensing base can provide a calendar feature, an inventory feature, a data feature, a reorder feature, and a settings feature, each of which will be discussed in more detail below.

Figure 2:
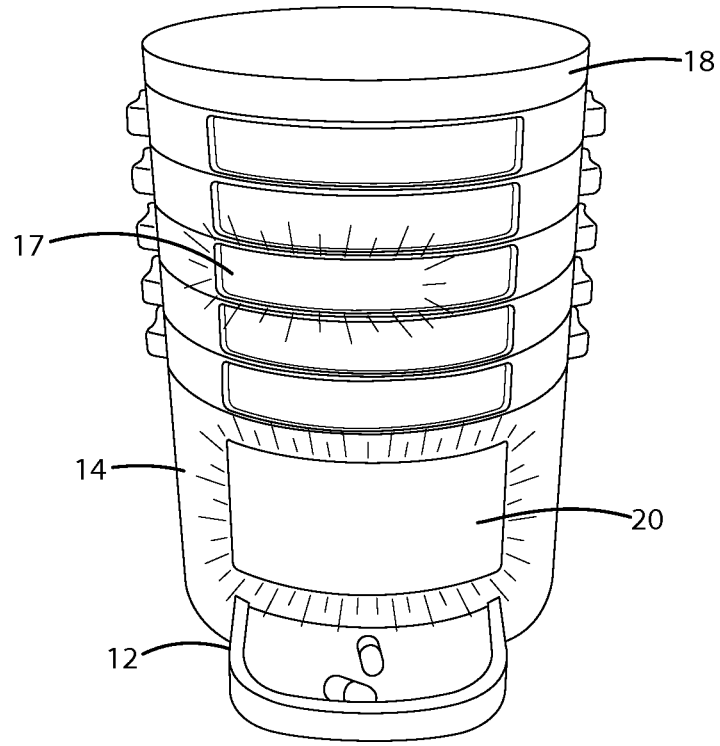
FIG. 2 is a perspective view of the dispenser system with a reminder showing time to dispense a pill.
Figure 3:
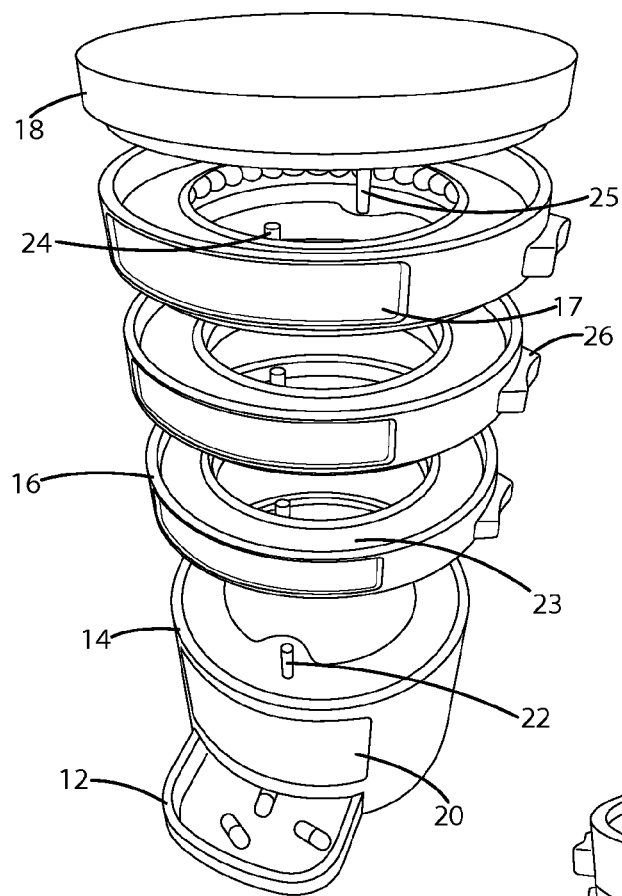
FIG. 3 is an exploded perspective view of the dispenser system.
Figure 4:
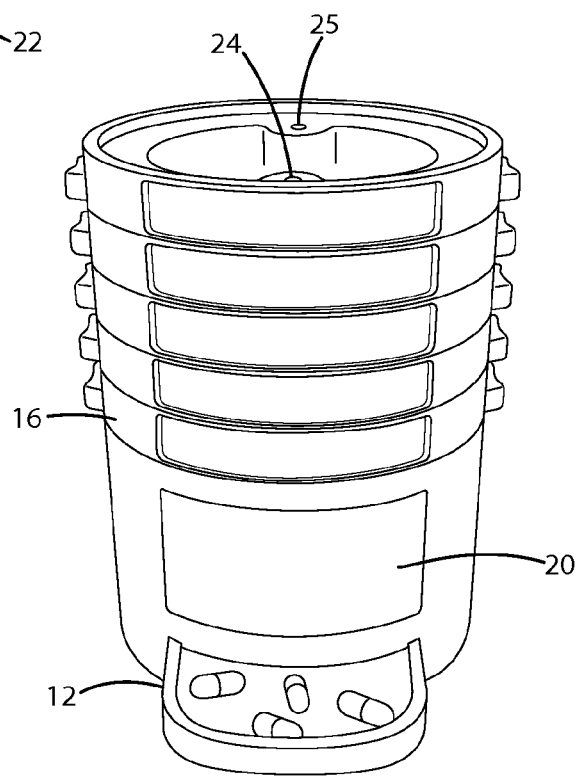
FIG. 4 is a perspective view of the dispenser system with the cap removed.

The display 20 can also be used to remind a user when it is time to take a certain medication. For example, in FIG. 2, the display can include a message indicating that it is time for the user to take their medication or supplement. Reminder messages and other information on the display 20 can be coordinated with the aesthetic look and feel of the package 16 including the package display 17 or label if one is provided. For example, as shown in FIG. 2 the dispensing system display 20 can be lit in the same color as the package display 17.

The dispenser base 14 can be coupled to a power source, such as an electrical connection to a wall socket or a battery. In alternative embodiment, the dispenser base 14 can be powered wirelessly by induction. Electrical power can be distributed from the dispensing system to the various packages 16 via an electrical connection. In the current embodiment, the dispenser base 14 includes two pins 22, 23 for transferring power to the packages 16. Each package 16 also includes two pins 24, 25. When the first package 16 is stacked on the dispenser base 14, the two pins 22, 23 from the dispenser base form an electrical connection with the two pins 24, 25 from the first package 16. As each successive package 16 is stacked on top of the previous package, the two pins 24, 25 from the bottom package form an electrical connection with the two pins 24, 25 from the top package. In this way, electrical energy can be provided to each of the packages from the dispenser base 14. In alternative embodiments, the packages 16 can be powered in a different way. For example, each of the packages 16 may include a coil and the dispenser base or an inductive charger may inductively power the packages 16, each of the packages can include a battery, or the electrical connection with the dispenser system 14 can be formed in a different way than described in the current embodiment. In some alternative embodiments, some or all of the packages 16 can be unpowered.

The control system can implement one or two way communication can be implemented between the dispenser system 14 and the packages 16. For example, in the current embodiment, the pins 22-25 provide an electrical connection for both power transfer and communication. Communication can be modulated on top of the electrical power signal, or, electrical communication and power can be provided mutually exclusively using a communication and power protocol to control when power is transferred and when communication can occur. In one embodiment, each package or type of package includes a unique identifier that can be utilized to uniquely communicate with that package or type of package. For example, the dispenser system 14 can broadcast a message to all packages, but only the package or packages with the matching identifier process the message. In another embodiment, the dispenser system 14 and packages 16 can share a common pin and additional pins can provide a physical address scheme. For example, pins 22 and 24 can be replaced with multiple pins. For the sake of providing an example, perhaps five address pins are provided. The electrical circuit in each package 16 can be connected to one or more of the five pins, which electrical connections are made would form the address to that package. For example, one pin may be connected to the package 16 electronics and the other four pins may simply provide a pass-through signal. Additional addresses can be provided by connecting multiple of the pins to the package 16 electronics. In this way, a large number of addresses can be provided with a limited number of pins. Various addressing schemes can be utilized to address multiple packages 16 simultaneously. For example, some packages can include multiple addresses, one address for being selected alone and separate addresses for being selected in combination with another package or packages. In alternative embodiments, communication may be implemented via a separate communication connection, such as RFID or another wireless communication technology, which will be described in more detail below.

Figure 5:
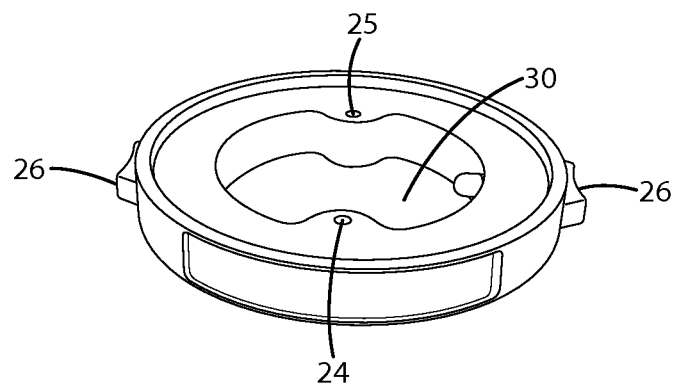
FIG. 5 is a perspective view of a plurality of packages in accordance with one embodiment of the present invention.
Figure 6:
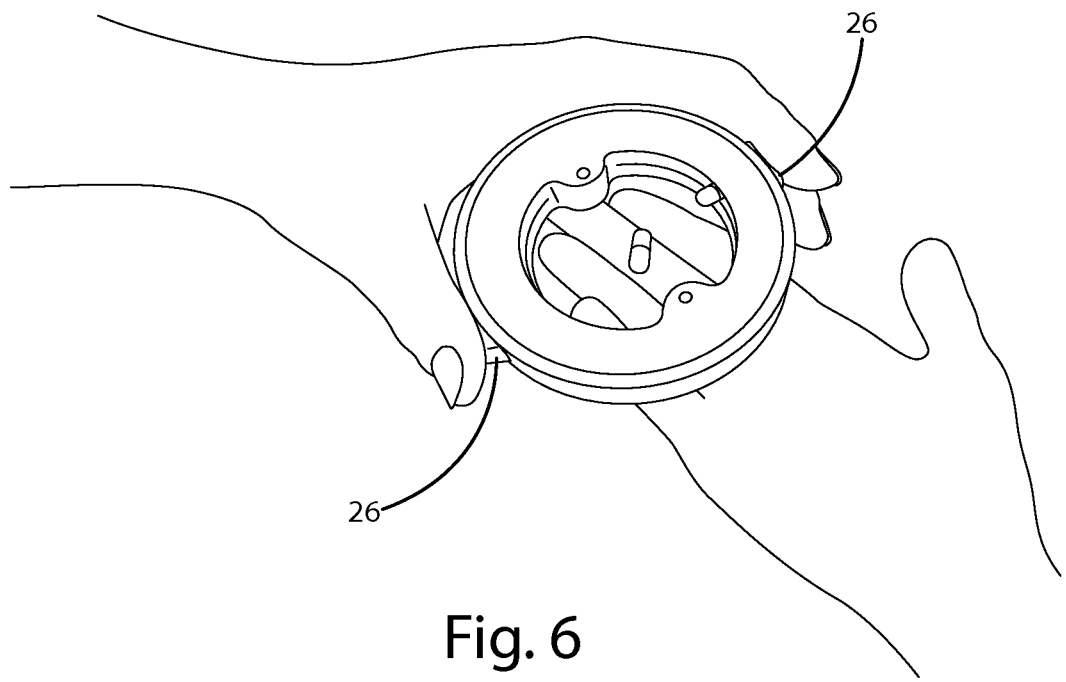
FIG. 6 is a perspective view of a package being manually operated to dispense a pill.

Referring to FIGS. 5 and 6, a package is shown separated from the dispenser base in order to illustrate how a pill can be dispensed from a package. The pills are arranged annularly about the edge of the package. The dispensing element 26 acts to dispense a pill from the package 16 into the center hole 30 in the package. When the package 16 is installed on the dispenser system 10, the pill drops through a similar hole 30 in any other installed packages, through a hole in the dispenser base 14, and eventually is dispensed via the dispenser tray 12.

Figure 7:
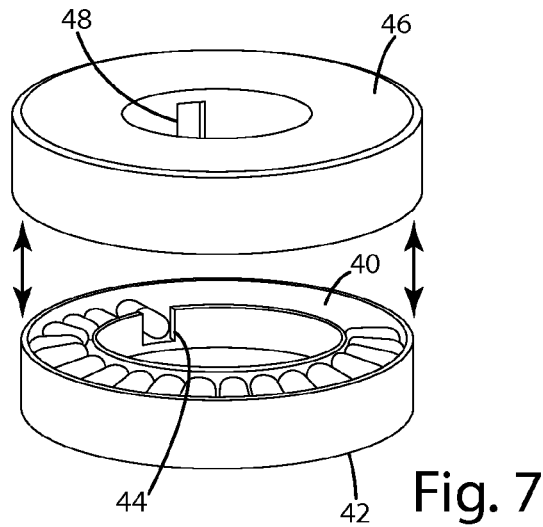
FIG. 7 is an exploded perspective view of an alternative embodiment of a package.

Referring to FIG. 7, the package 16 can be an assembly including a bottom housing portion 42 that holds the pills in an annular channel 40 having a dispensing channel 44 where a pill can be dispensed via a dispensing element (not shown) and a top housing portion 46 that also includes a dispensing channel 48.

A number of different dispenser elements 26 are described in FIGS. 8-16. This list of dispenser elements is not meant to be exhaustive, but rather is merely exemplary. In fact, additional exemplary dispenser elements are described elsewhere in the application in connection with other alternative embodiments.

Figure 8:
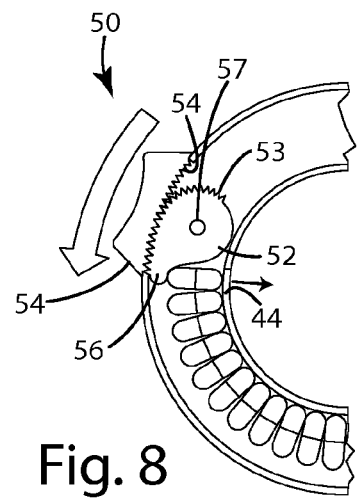
FIG. 8 is an alternative embodiment of a mechanism for dispensing pills from a package.

FIG. 8 illustrates a ratchet dispensing element 50. The ratchet dispensing element 50 includes a ratchet 52 and a friction element 54. A user can operate the ratchet by sliding a friction element 54 over the ratchet 52. The friction element teeth 55 can interact with the ratchet teeth 53 to rotate the ratchet 52 about a pivot 57. As the ratchet 52 rotates, the ratchet end 56 engages a pill and forces it out the dispensing channel 44. The ratchet can be manually returned to a home position or in an alternative embodiment, a spring can be provided that automatically returns the friction element 54 to a home position so that the next pill can be moved into dispensing position.

Figure 9:
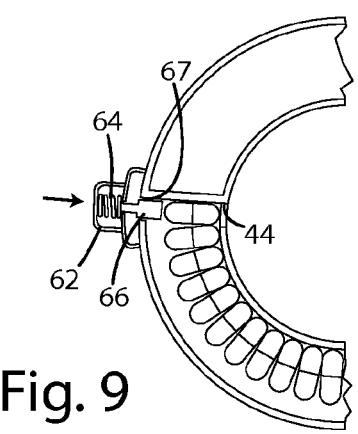
FIG. 9 is an alternative embodiment of a mechanism for dispensing pills from a package.

FIG. 9 illustrates a snap release dispensing element 60. The snap release dispensing element 60 includes a button 62, a spring 64, and a plunger 66. In a home position, the plunger 66 is friction fit with a plunger channel 67 in the side wall of the package 16. When the button 62 is actuated, the spring 64 is compressed, and the plunger 66 overcomes the friction fit with the plunger channel 67 in such a way that it snaps through the plunger channel 67 and forces a pill in the dispensing position through the dispensing channel 44. After the button 62 is released, the tension from the compressed spring 64 releases and pulls the plunger 66 back through the plunger channel 67 so that the next pill can be moved into dispensing position.

Figure 10:
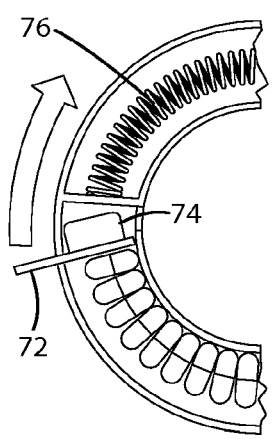
FIG. 10 is an alternative embodiment of a mechanism for dispensing pills from a package.
Figure 17:
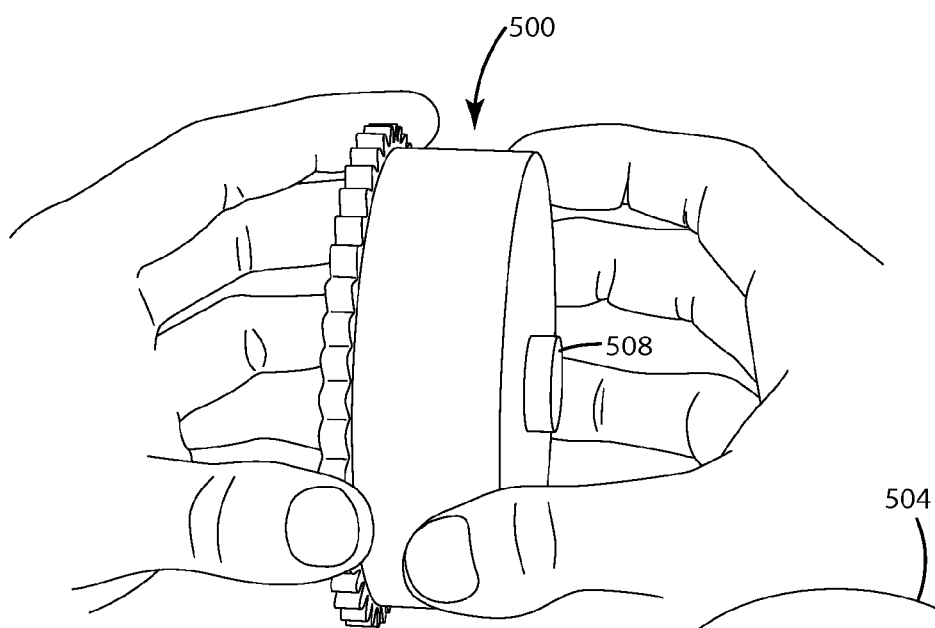
FIG. 17 is an alternative embodiment of a package.
Figure 18:
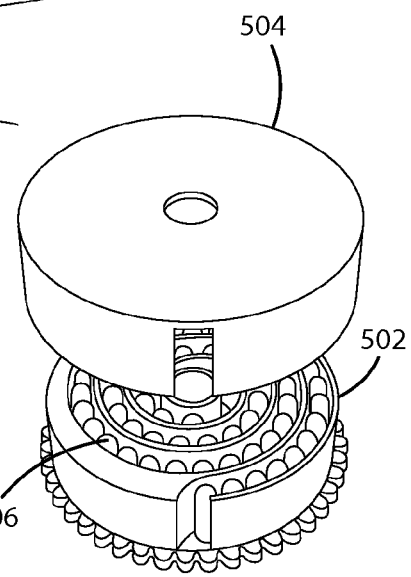
FIG. 18 is an exploded view of the package of FIG. 17

FIG. 10 illustrates a slide and hole dispensing element 70. The slide and hole dispensing element 70 includes a slideable stop 72 and a hole 74. In one position the slideable stop 72 prevents a pill from exiting the package 16 through the hole 74. When slid into a second position, the slideable stop no longer prevents the pill from exiting through the hole 74. A spring 76 can be included such that sliding the stop 72 also results in a pill being urged in the direction of the hole 74. The hole 74 may lead to a ramp such that the pill exits the package towards the center in a similar manner to other packages described herein.

Figure 11:
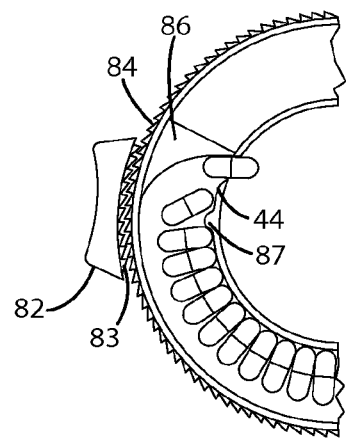
FIG. 11 is an alternative embodiment of a mechanism for dispensing pills from a package.

FIG. 11 illustrates a ratchet and ramp dispensing element 80. The ratchet and ramp dispensing element 80 includes a friction element 82, ratchet teeth 84 along a side wall of the package 16, and a ramp 86. The friction element 82 includes ratchet teeth 83 that interact with the ratchet teeth 84 on the side wall of the package. As the friction element 82 is slid, the ratchet teeth 83 engage the ratchet teeth of the side wall and rotate the package relative to the ramp 86. The portion that is rotating includes the pills, which engage the stationary ramp and are forced to exit the package as the friction element 84 is slid. A stationary notch 87 can be provided to provide an amount of friction that can be felt as each pill engages the notch while the friction element 82 is being rotated. This provides feedback to the user about when a pill is being dispensed as they rotate the friction element 82.

FIGS. 12A and 12B illustrate rotating gear dispenser elements. In FIGS. 12A and 12B, the rotating gear dispenser 90 is located within the path of the pills in the package in such a way that the gear is externally accessible and the pills are routed into a dispensing position such that actuating the gear forces the pills through the dispensing channel 44. In FIG. 12A, the dispensing channel 44 is located on the inside wall of the package 16. In FIG. 12B, the dispensing channel 44 is located on the outside wall of the package 16. In FIG. 12A, a wall 92 may provided so that pills are urged through the dispensing channel instead of further along in the package. The gear 90 can be positioned such that the gear clears the wall, but still engages the pills. Alternatively, the wall can have an aperture sized to fit the gear, but not the pills so that the gear can rotate through the wall, but pills are impeded by the wall. In FIG. 12B, the rotating gear dispenser is located within the path of the pills in the package in such a way that the gear is externally accessible and the pills are routed into a dispensing position such that actuating the gear forces the pills. A similar wall may be provided in the FIG. 12B embodiment as well.

FIG. 13A illustrates two pivot arm dispenser element embodiments. In these embodiments, a pivot arm 100 is provided that engages a pill and urges it through a dispensing channel 44. In one embodiment, the pivot arm 100 includes an pill engaging portion 102 and a handle portion 104. A user can pivot the pivot arm 100 by pulling the handle portion 104 away from the exterior wall of the package 16. As the pivot arm pivots, the pill engaging portion 102 engages a pill and urges it through the dispensing channel 44. A spring or other element that provides a return force may be implemented to return the pivot element to a home position. In another embodiment, shown in FIG. 13B, the pivot arm 100 is located within a button 106, such that when the button 106 is depressed, the button engages the pivot arm 100 and the pill engaging portion 102 of the pivot arm engages the pill and urges it through the dispensing channel 44.

The dispenser base 14 and packages 16 need not be arranged vertically. For example, in one embodiment the dispenser base 14 and packages 16 can be arranged horizontally. In the illustrated embodiment, a pill can be dispensed by lifting a package. For example, one embodiment of a push back dispenser element is illustrated in FIGS. 15A-15B. In FIG. 15A a package with pills inside is shown in a home position. FIG. 15B illustrates a pill being dispensed. As the top housing 112 is rotated a dispensing channel 44 is opened so that a pill can fall out via gravity and be urged towards the dispensing area 116 by a ramp 114 that is formed by how the housing 112 is lifted.

FIG. 16 illustrates another horizontal configuration. In this embodiment, pills are arranged within tablet dispensers or packages 16 and actuating the tablet dispenser dispenses a pill. An exemplary tablet dispenser is disclosed in U.S. Pat. No. 4,966,305 entitled tablet dispenser and is herein incorporated in its entirety.

The above embodiments discuss a variety of dispenser elements that allow a user to control the dispensing of the contents of the packages. Although not discussed in connection with each of the above embodiments, essentially any embodiment can include structure that moves the contents of the package into dispensing position so that actuation of the dispensing element results in some of the contents of the package being dispensed. For example, whenever a pill is dispensed, the next pill to be dispensed can be moved into position using a spring or other mechanism.

Figure 19:
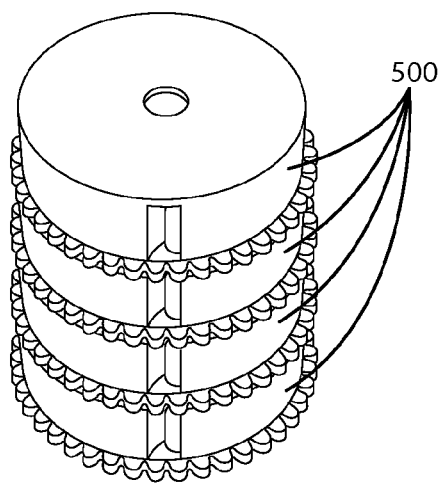
FIG. 19 is a plurality of packages of FIG. 17 stacked vertically.
Figure 20:
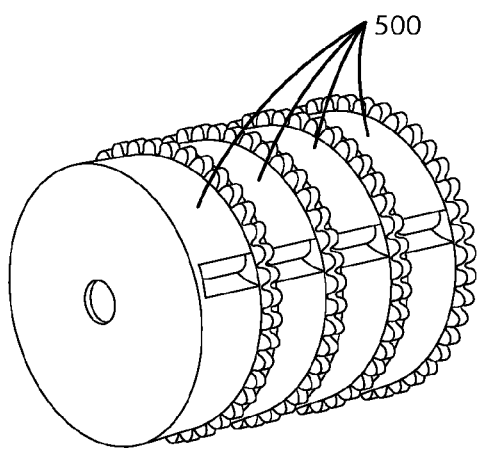
FIG. 20 is a plurality of packages of FIG. 17 stacked horizontally.

Another alternative embodiment of a package is shown in FIGS. 17-20. In this embodiment, the package 500 generally includes a bottle 502 for holding the pills and a gear cap 504 for closing the bottle 502 and assisting in dispensing the pills from the bottle 502 (See FIG. 17). As perhaps best shown in FIG. 18, the pills are vertically stacked in a spiral channel 506 in the bottle 502. In alternative embodiments, as shown in other drawings, the pills can be horizontally stacked. The gear cap 504 include a downwardly extending pin (not shown) that extends down into the spiral channel 506. When the package 500 is loaded, the pin (not shown) is positioned in the spiral channel 506 inwardly of the innermost pill. As the bottle 502 and gear cap 504 are rotated relative to one another in the proper direction, the pin follows the spiral channel 506 in an outward direction pushing the pills outwardly through the spiral channel 506, thereby causing the outermost pill to be dispensed from the package 500. The pin (not shown) is carried in a radially extending slide (not shown) so that the pin can move radially outward as the bottle 502 and gear cap 504 are rotated relative to one another. The bottle 502 and gear cap 504 may be provided with detents or other interacting features (not shown) that facilitates rotation of the package 500 in one-pill increments. For example, the interacting features may provide tactile feedback that allows a user to feel that the bottle 502 and gear cap 504 has been moved relative to one another in a one-pill increment. If the package is intended for use with pills that are taken in multiples (e.g. two at a time), the interacting feedback features may be disposed in the appropriate multiple-pill increments (e.g. a two-pill increment). Multiple packages 500 may be stacked together, for example, by the friction fit of a head 508 protruding from the top of the package 500 with a corresponding seat (not shown) defined in the bottom of the package 500. Referring now to FIG. 19, multiple packages 500 may be stacked vertically. Alternatively, multiple packages 500 may be stacked horizontally as shown in FIG. 20. The "geared" outer surface of the bottle 502 provides a mechanism to facilitate rotation of stacked packages 500.

Figure 21:
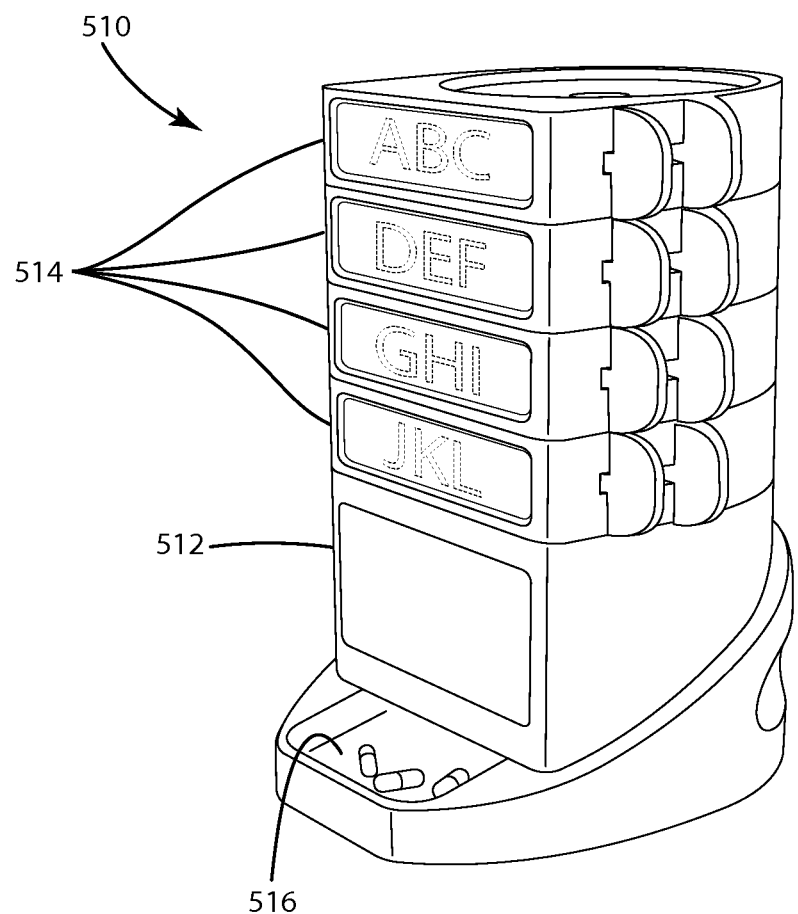
FIG. 21 is an alternative dispenser system.
Figure 22:
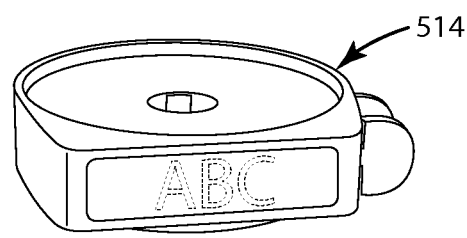
FIG. 22 is an alternative package.

An alternative dispenser system 510 is shown in FIGS. 21-22. In this embodiment, the dispenser system 510 generally includes a base 512 and one or more packages 514. The base 512 includes a control system (not shown) that interacts with packages 514 to provide controlled operation of the dispenser system 510. Except as described, the base 512 is generally identical to the base described above and therefore will not be described again in detail. In this embodiment, the packages include a mechanism that dispenses pills into the center of the packages 514, where they fall to the base 512 and are accessible in tray 516 (see FIG. 22).

A series of alternative mechanical designs for dispensing pills from a package are shown in FIGS. 23-30. FIGS. 23 and 24 show an embodiment that is similar to the mechanism used in a gum-ball machine. The package 520 includes a reservoir 522 for storing pills and an arm 524 for moving pills toward a reservoir outlet 526. The arm 524 may be biased by a spring 528 or other mechanism. The package 520 includes a chute 530 for reorienting the pills into alignment with the reservoir outlet 526 for dispensing. A reciprocating carrier 532 is positioned below the reservoir outlet 526 for selectively moving one pill at a time from the reservoir outlet 526 to the package outlet 534. The carrier 532 defines an opening 536 that corresponds to the shape of a single pill. In operation, the carrier 532 is positioned with its opening 536 below the reservoir outlet 526. This allows a pill to fall into the opening 536. The carrier 532 is then rotated to move the opening 536 into alignment with the package outlet 534. As the carrier 532 is moved, it shuttles the pill to the package outlet 534 where it may fall by gravity out of the package 520. In dispensing from a single package 520, the pill may be dispensed directly into a users hand. When dispensing from a dispenser system, the packages 520 may be positioned so that their package outlets 534 are aligned. As a result, a pill dispensed from one package will fall through the package outlets 534 of all of the underlying packages until it reaches the dispenser system tray, where it can be removed manually.

FIGS. 25A-B show an alternative embodiment in that package 540 includes a bottle 542 with a rotating spiral 544 and a slider 546. As the spiral is rotated, one pill after another becomes aligned with the opening 548 in the slider 546. The slider 546 is capable of outward radial movement so that the opening 548 remains in alignment with the pills as they spiral outwardly from the center.

FIGS. 26A-B show an alternative embodiment of a package 550 with a reciprocating plunger 552 for rotating the pills and a stationary ramp (not shown) for pushing pills out through the center as they are rotated. The bottle 554 includes a ratchet raceway 556 with opposed cooperating ratchet surfaces. In this embodiment, the plunger 552 is coupled to a pawl 554 operatively positioned in the raceway 556. When the plunger 552 is pushed in, the pawl 554 engages a ratcheting surface on one side of the raceway 556 forcing the bottle 554 to index in a one-half pill increment. When the plunger 552 is released, it is forced back out by a spring or other biasing mechanism (not shown). This movement of the plunger 552 causes the plunger to travel back across the raceway 556 and engage a ratcheting surface on the opposite side, thereby forcing the bottle 554 to index in another one-half pill increment. As a result, the inward and outward movement of the plunger 552 cause the bottle 554 to index in a one-pill increment. This cause the entire stack of pills to rotate into the ramp the distance of one pill. The ramp forces the pill out of the bottle 554 and into the open center, where it can fall to a users hand or into the dispensing tray of a dispenser system.

FIGS. 27A-B show an alternative embodiment of the mechanism shown in FIGS. 26A-B. In this embodiment, the package 560 includes the same general mechanism as the package of FIGS. 26A-B, except that there is a second ring of pills 562 positioned atop the first ring. When a pill is dispensed from the bottom ring of pills, the pill positioned above it in the second ring of pills will be able to fall by gravity down into the first ring of pills to take the place of the dispensed pill.

FIGS. 28A-C show an alternative package 570 in which there is a reservoir 572 for storing loose pills. The reservoir 572 may include a central cone 574 for causing pills to the outside of the package into individual pill locations. In this embodiment, the pills may be moved from the individual pill locations using the mechanism described above in connection with the embodiment of FIGS. 27A-B. FIG. 28C shows the cone 574 and the space 576 for the individual pills to fall.

FIGS. 29A-B show a package 580 that is an alternative embodiment of the package of FIG. 28A-C. In this embodiment, the reservoir 582 and cone 584 cause loose pills to fall into down into individual pill carrier slots 586. FIG. 29B shows the package 580 with the cover removed to show the internal mechanism. As perhaps best shown in FIG. 29B, the carrier slots 586 are defined by a pair of spaced-apart indexing rings 588. FIG. 29B shows the pills above the carrier slots 586 for purposes of disclosure, but it should be understood that the pills will fall by gravity down into the carrier slots 586. As the indexing rings 588 are rotated, the pills will engage the ramp 590 and be pushed out of the package 580 for use. The package 580 may includes a lever 592 and ratchet arrangement 594 for causing the indexing rings 588 to rotate in one-pill increments.

Figure 30:
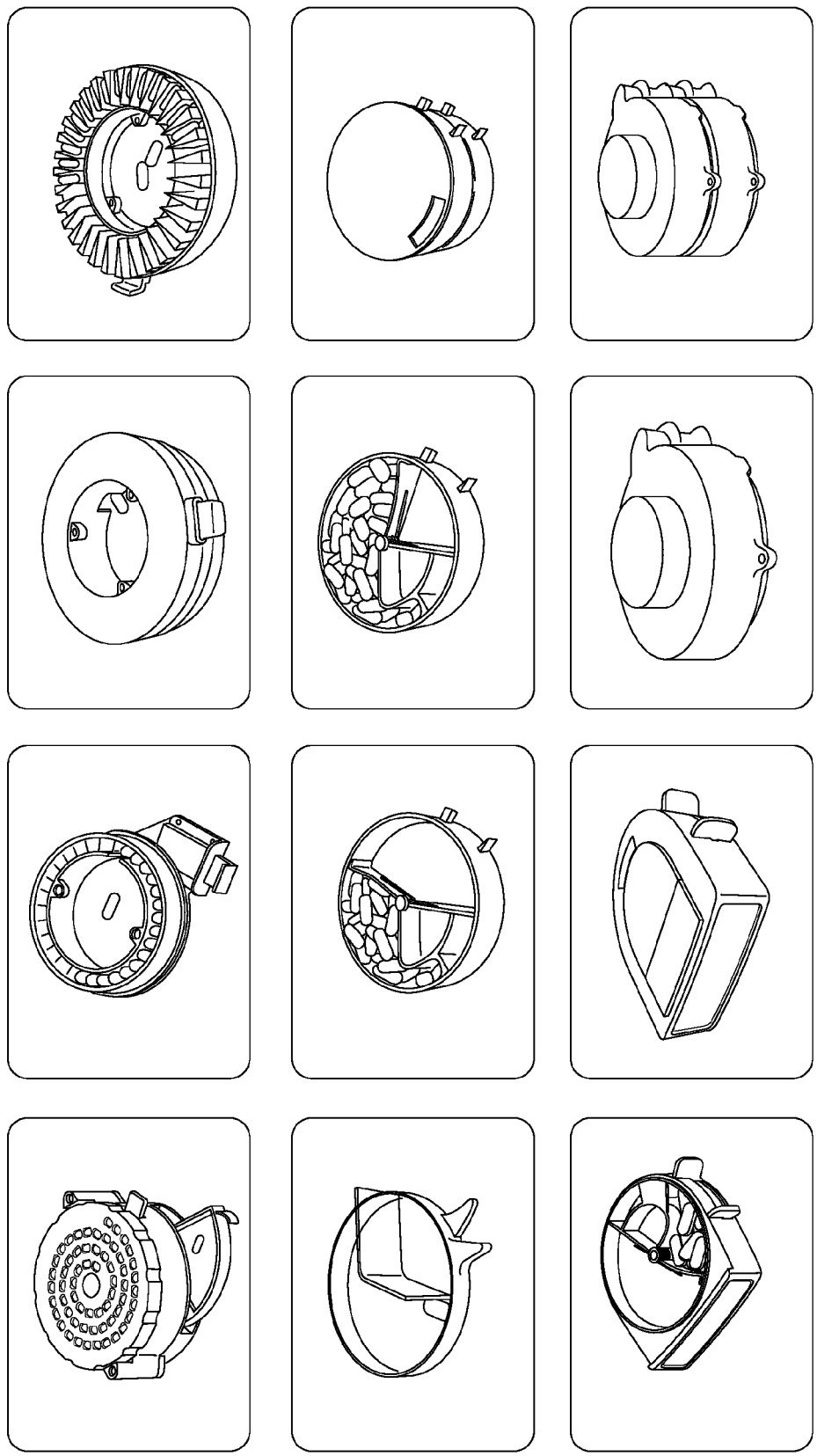
FIG. 30 includes photographs of various prototypes of alternative packages.

FIG. 30 shows illustrations of a plurality of prototypes of different packages or package mechanisms.

Figure 31:
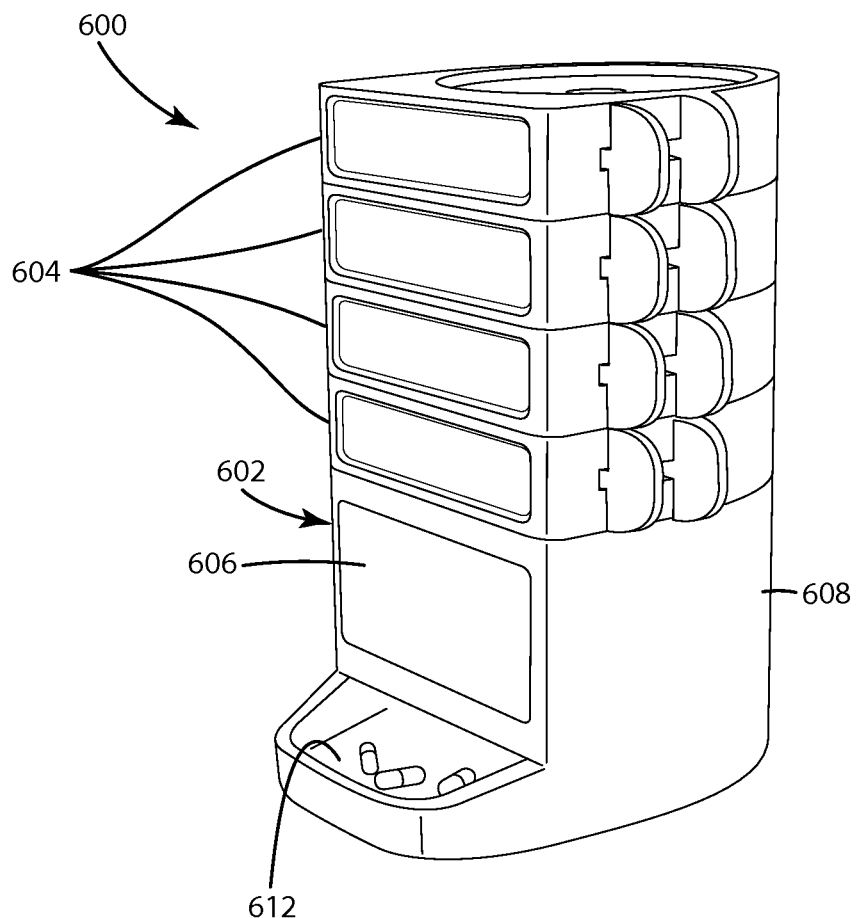
FIG. 31 is an alternative dispenser system.
Figure 32:
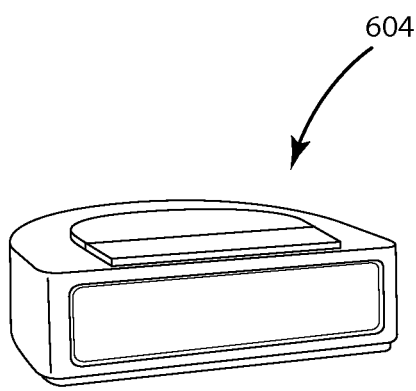
FIG. 32 is a perspective view of a plurality of alternative packages.
Figure 33:
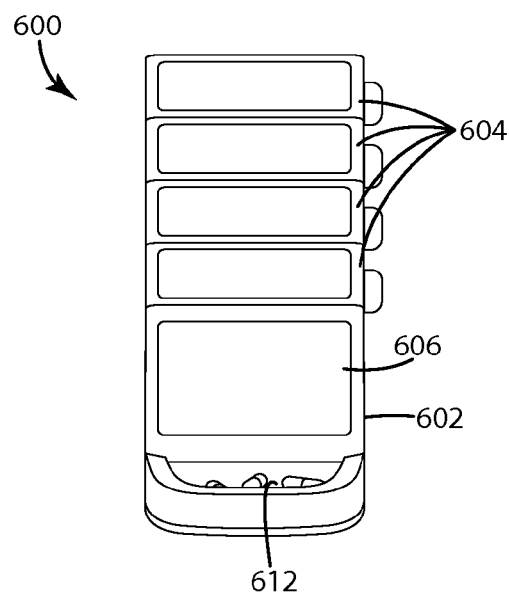
FIG. 33 is a front view of the dispenser system of FIG. 31.
Figure 34:
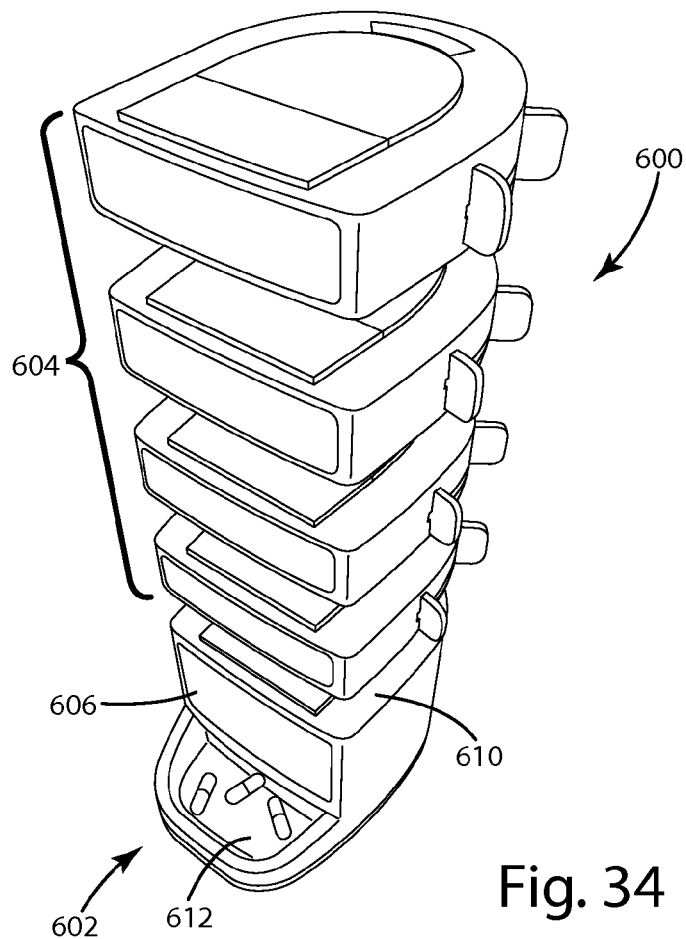
FIG. 34 is an exploded perspective view of the dispenser system of FIG. 31.
Figure 35:
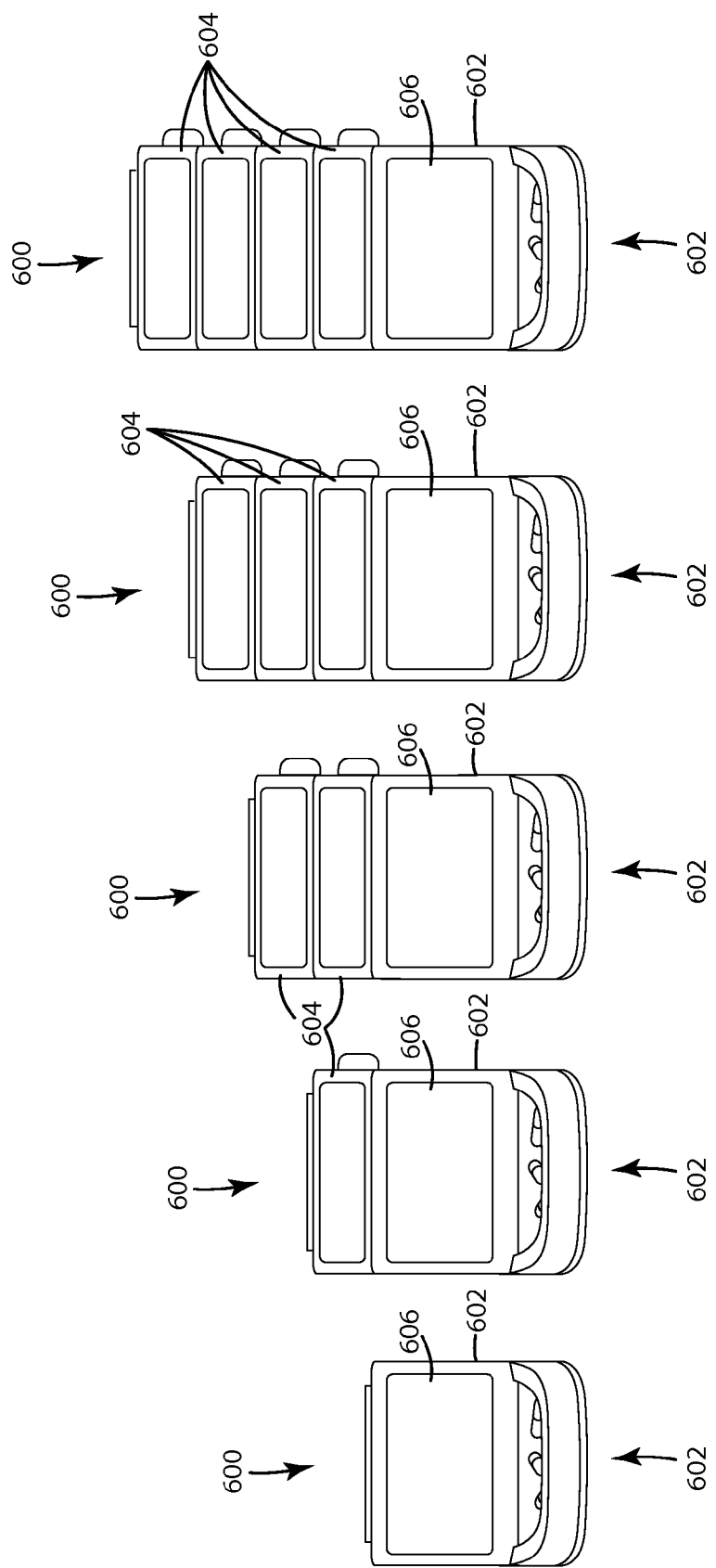
FIG. 35 shows the dispenser system of FIG. 31 with different numbers of installed packages.

FIGS. 31-47 show another alternative embodiment of the present invention. In this embodiment, the dispenser system 600 includes a base 602 and one or more packages 604. The packages 604 are configured so that they can be manually operated to dispense pills without a base 602 or they may be stacked on a base 602 to allow dispensing to be coordinated and tracked by the base 602. FIG. 31 shows four packages 604 stacked on base 602. Each of the packages 604 shown in FIG. 31 contain a different type of pill, but that is not strictly necessary. FIG. 33 shows a front view of the dispenser system 600 and FIG. 34 shows a partially exploded view with the packages 604 spaced apart above the base 602. FIG. 35 shows the dispenser system 600 with different numbers of packages 604. As can be seen, the packages 604 may be stacked on the base 602 one atop the other. Although FIG. 35 shows up to four packages 604 on the base 602, it should be understood that the base 602 may be configured to receive even more packages 604, if desired. Additional illustrations of the dispenser system 600 are shown in FIGS. 42-44.

The base 602 generally includes a housing 608 that houses control system (not shown) and a touch screen 606. The housing 608 defines a pedestal 610 to receive one or more packages 608 and a dispenser tray 612 to hold dispensed pills before they are consumed by a user. The pedestal 610 may be contoured to correspond with the bottom surface of a package 604. For example, in the illustrated embodiment, the pedestal 620 is recessed and the bottom surface of each package 604 is extruded so that the bottom surface of the package 604 fits closely into the recess in the pedestal. The top surface of each package 604 may also be contoured to interfit with the bottom surface of any package that may be stacked above. The pedestal 620 may have a through-hole (not shown) that extends from the pedestal to the tray 612. The through-hole may be positioned to align with the package outlets in the stacked packages so that pills dispensed from the packages 604 will fall down into the through-hole and eventually into the dispenser tray 612. The dispenser tray 612 may have a forwardly slanted floor so that dispensed pills have a tendency to roll forward where they are accessible to a user.

The control system controls operation of the dispenser system 600, and generally includes a communication subsystem, a tracking subsystem and a reordering subsystem that are described in more detail below. The communication subsystem has the ability to communicate with the packages to obtain package information. This communication may be one-way or two-way. The packages may be provided with information relating to the packaged pills or to the use of the packaged pills. The package can store essentially any information that could be relevant to the pills, use of the pills or the dispensing system, such as pill type, prescribed dosage, consumption frequency, manufacturer, manufacturing date, consumer name, phone numbers, prescription number, dates, consumer addresses, pharmacy and store addresses, number of refills, refill dates, doctor names, product quantity, warnings, laws, side effects, expiration dates, barcodes, and recommendations. In the illustrated embodiment, the packages 604 are provided with an identification of the product type stored in the package, the number of pills in the package and information about when it is to be taken. The packages 604 may also include additional information, if desired. By reading the information from each package 604, the dispenser system 600 knows what is in the package 604, when it is to be taken and can understand and track inventory. Each package may be loaded with appropriate information at essentially any suitable time. For example, each package may be loaded with the desired information when it is filled with pills at the pharmacy or other dispensing facility.

In this embodiment, the dispenser system is configured to obtain information from the packages using an RFID system (See FIG. 46). However, the system may use essentially any data transfer methods and apparatus, whether wired or wireless. For example, the dispenser system may obtain information from the packages using hardwire communication schemes (such as pins 22, 23, 24 and 25 discussed above), Bluetooth, low power RF data transmission or WiFi. In this embodiment, the packages 604 each include an RFID chip containing the desired information. The RFID chips can be polled by the communication subsystem to collect the information from the packages. As an alternative to RFID chips, each package 604 could include a controller with memory for storing the desired information.

In some embodiments, it may be desirable to provide power to the packages 604. For example, the packages 604 may include LED's or other mechanisms that rely on electrical power. This power may be routed to the packages 604 using the pin arrangements discussed above. However, in an alternative embodiment, the packages 604 may wirelessly receive power from the dispenser system 600. For example, the dispenser base 602 may have a primary that produces a time-varying electromagnetic field and the packages 604 may each include a secondary in which power is induced by the time-varying electromagnetic field. In this alternative embodiment, the dispenser base 602 and packages 604 may exchange communications using communication signals overlaid onto the time-varying electromagnetic field. For example, in this wirelessly powered alternative system, the packages 604 and dispenser base 602 may communication using backscatter modulation.

The control system may read information from or write information to the packages 604 in realtime as desired. For example, in the illustrated embodiment, the dispenser system 600 may read information from each package 604 when it is first stacked on the dispenser base 602 as shown in FIG. 46. The dispenser system 600 may additionally or alternatively periodically poll the packages 604 to periodically obtain information about the installed packages 604. This may permit the control system to determine when a package 604 is removed. The control system may maintain inventory and usage information in memory onboard the packages 604. This may facilitate accurate tracking when packages are removed and replaced or moved from one dispenser base 602 to another.

The control system tracking subsystem is configured to use the information obtained from the packages 604 to determine the appropriate dispensing schedule. For example, the tracking subsystem may obtain the first dispensing time for each pill from its package 604 and may calculate additional dispensing times based on a time interval obtained from the package 604. The tracking subsystem includes an internal clock for carrying out these functions. The tracking subsystem may track inventory by obtaining information concerning the dispensing of pills and making appropriate adjustments to inventory counters stored in memory. When it is time to dispense a pill, the tracking subsystem may provide a reminder to the user. The reminder may be a message displayed on a screen incorporated into the base 602. The reminder may additionally or alternatively include a message sent to an electronic device, such as a smart phone, tablet or other hand held electronic device. The message may be an email, a text message or some other form of message. If desired, the dispenser system 600 may be provided with the ability to communicate directly with an electronic device to send reminders and other desired information. For example, the system may be able to communicate with a smart phone or tablet computer using Bluetooth, WiFi, Near Field Communications or essentially any other type of wireless communications.

Referring now to FIG. 47, the packages 604 may be provided with the ability to illuminate to assist a user in dispensing the correct pill. For example, the tracking mechanism may direct the appropriate package 604 to illuminate an internal light (e.g. one or more LEDs) to provide a visual indication of which pill is to be dispensed. This direction may be sent from the base 602 to the appropriate package 604 using the same communications methods and apparatus used to obtain information from the packages 604. This may be done in a wired or wireless scheme. It may be desirable to use a hardwired or wireless power transfer system to transmit sufficient power to the packages 604 to allow them to illuminate the internal light.

The dispenser system 600 of this embodiment tracks pill dispensing information. For example, the dispenser system 600 may maintain inventory of the pills in the various installed packages 604. The dispenser system may use this information to provide inventory information, warn of low inventory and/or provide reordering capabilities. The dispenser system is also able to monitor user statistics like when it dispenses pills and how often it dispenses. The time and date associate with each pill being dispensed may be recorded in data file. For some medications with deadly side effects, the dispenser system 600 can limit the number of pills taken at once and the time in between the next dose.

The tracking subsystem may determine when a pill is dispensed by obtaining information about actuation of the dispensing mechanisms in the various packages. In this illustrated embodiment, operation of the dispensing mechanisms may be determined by the packages 604 and reported to the base 602. For example, each package 604 may includes a pair of contacts that are opened/closed as the dispensing mechanism is operated. The package 604 may include an internal controller that monitors the status of these contacts to recognize when a pill is dispensed. Again, communications from the packages 604 to the base 602 may be made using the same communications methods and apparatus used to obtain information from the packages 604. In some applications, it may be desirable to supplement or replace the aforementioned method with a sensor that confirms dispensing of a pill. For example, the base 602 may include an optical sensor or a weight sensor that determines whether a pill has been dispensed. The optical sensor may include an IR transmitter and an IR sensor arranged on opposite sides of the through-hole in the base (e.g. the path through which the pills must fall from the packages 604 to the dispenser tray 612). The action of a pill falling between the transmitter and sensor can allow the system to recognize that a pill has been dispensed. The optical sensor information can be coupled with information from a package 604 concerning the actuation of the dispensing mechanism to confirm that a pill was dispensed and which package 604 it was dispensed from. For example, when the optical sensor goes off, the control system can query to the packages 604 to determine which package 604 was just actuated.

The reordering subsystem may be configured to allow automated pill reordering using a network. The network may be the Internet or some other network allowing for communication between the dispenser system 600 and the reordering facility (e.g. a pharmacy, medical dispensing facility or a food supplement supplier). In the illustrated embodiment, the dispenser system may be configured to provide reordering information via the network to the appropriate entity for supplying the depleted pills. The reordering subsystem may be activated by the tracking subsystem when the inventory information shows that it is time to reorder pills. For example, the dispenser system may warn the user that inventory is getting low and may request authorization from the user to order pills to restock the inventory. Upon authorization, the dispenser system may place an order over the network. As another example of a reordering system, the dispenser system may be configured to automatically reorder pills when the inventory is sufficiently depleted.

The tracking subsystem may also be configured to communicate pill usage information to a doctor, physician, pharmacist or other health specialist. Similarly, with food supplements, the dispenser system may communication pill usage information to a food supplement representative. This information may be used by the recipient for a wide variety of purposes, such as to counsel the user on possible changes in usage habits. For example, if the pills are not being taken on a timely basis the recipient may be able to counsel the user to improve. This information may also allow the recipient to make recommendations on additional or alternative pills that might be beneficial for the user.

Figure 45:
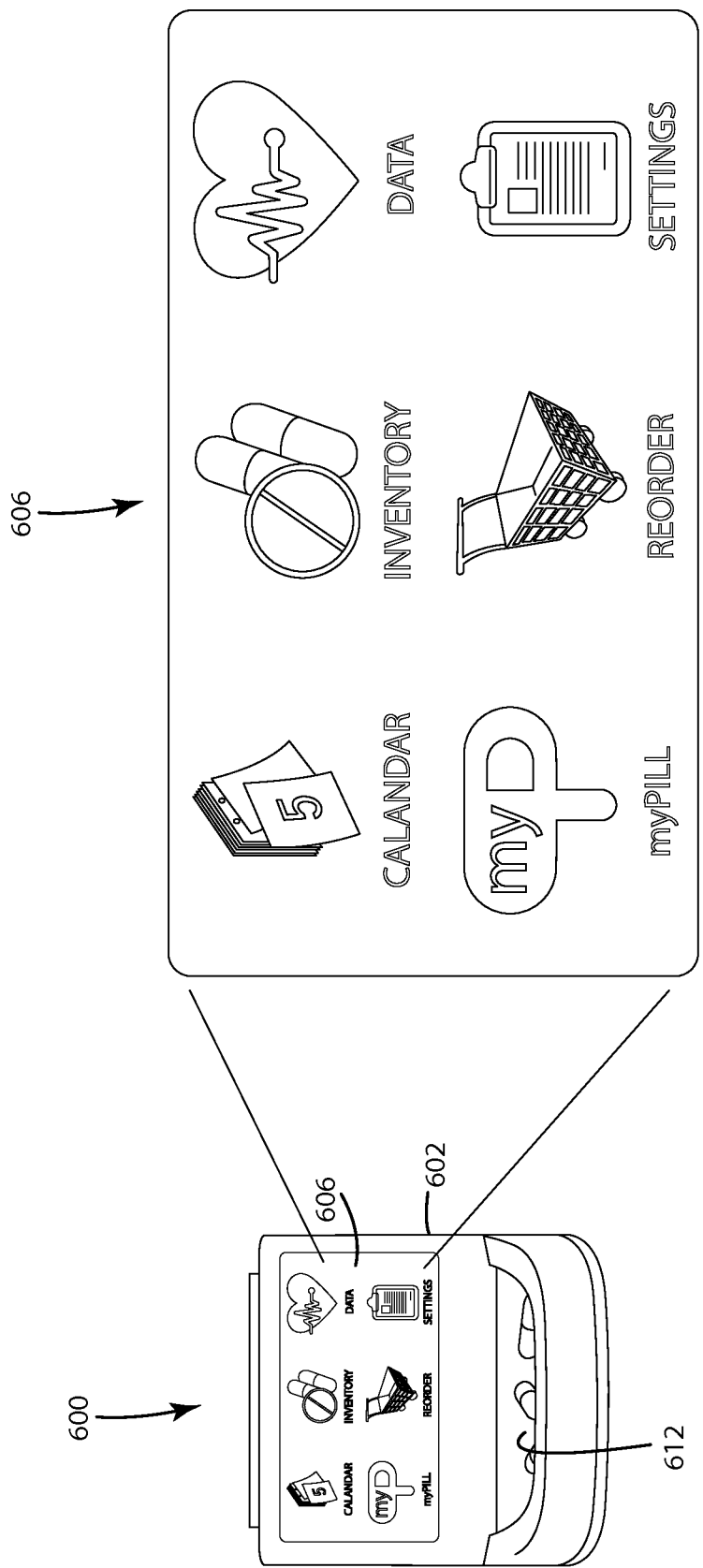
FIG. 45 is a enlarged view of a control system.

The base 602 may include a user interface to receive input and send output to a user. In the illustrated embodiment, the user interface is a touch screen 606 that allows a user to navigate through a graphical user interface that control operation of the dispenser system 600 and related functions. The user interface may vary from application to application, but the general operation of the user interface of the embodiment of dispenser system 600 will be generally described for purposes of disclosure. Referring now to FIG. 45, the touch screen 606 of this embodiment includes a main screen that contains a series of icon that provides a variety of options. The calendar icon may be pressed by the user to gain access to the upcoming schedule for dispensing pills. The inventory icon may be pressed to obtain inventory information on the pills in the packages 604. The data icon may be pressed to gain access to pill usage information, such as prior dispensing activities. The reorder icon may provide access to a system for reordering pills as desired by the user. The settings icon may be pressed to allow a user to configure the dispenser system, such as set the time, enter product reordering information, establish network connections, etc.

Figure 36:
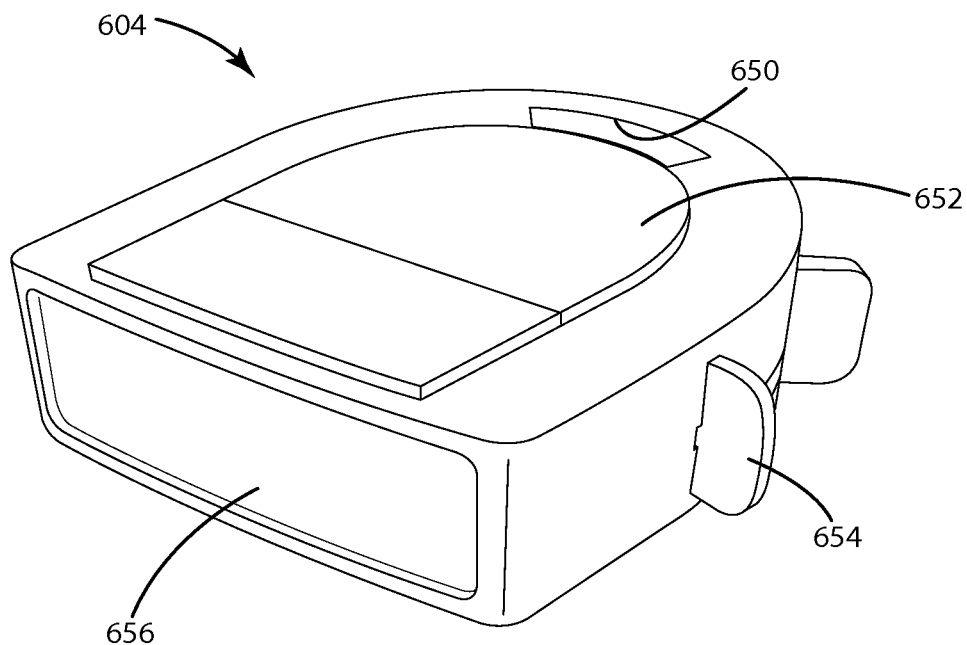
FIG. 36 is a perspective view of a package.

A more detailed description of packages 604 will now be provided with reference to FIGS. 36-41. FIG. 36 is a perspective view of a package 603 showing the package outlet 650 (or eject location), the raised top 652, the pill dispensing button 654 (or eject button) and a large front label 656. FIG. 41 shows an exploded view of the general components of the package 604, including bottom 660, indexing disc 662, main body 664 and top 668. The bottom 660 closes the bottom of the package 604 and may be recessed or extruded to interfit with the pedestal and the top surface of other packages. The indexing disc 662 is rotatable during operation to move a pill from the reservoir outlet (not show) to the package outlet 650 as described in more detail below. The indexing disc 662 includes a series of arcuate slots that align with screw bosses (not shown) for holding the bottom 660 to the main body 664. These arcuate slots allow the disc 662 to rotate despite the presence of stationary screw bosses joining the main body 664 and the bottom 660. The indexing disc 662 also defines a pill opening 680 that generally corresponds to the shape of one pill. As described below, the pill opening 680 receives a pill from the reservoir 670 and shuttles it to the package opening 650 as the disc 662 is rotated from the home position the eject position. The indexing disc 662 may include a void 682 to house spring for urging the indexing disc 662 into the home position. The indexing disc 662 also defines an eject hole 684 that aligns with the package opening 650 when the indexing disc 662 is in the home position. The eject hole 684 allows pills dispensed from above-stacked packages 604 to fall through the package 604 to the base 602.

Figure 37:
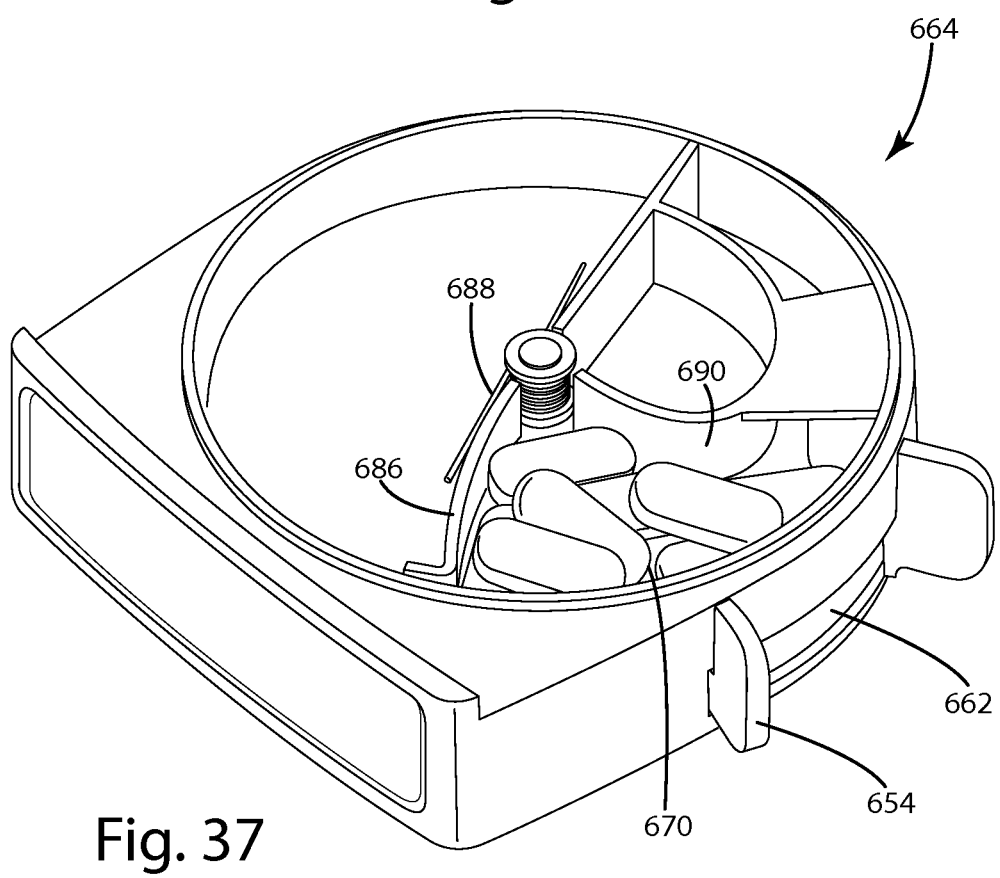
FIG. 37 is a perspective internal view of the package of FIG. 36.
Figures 38, 39:
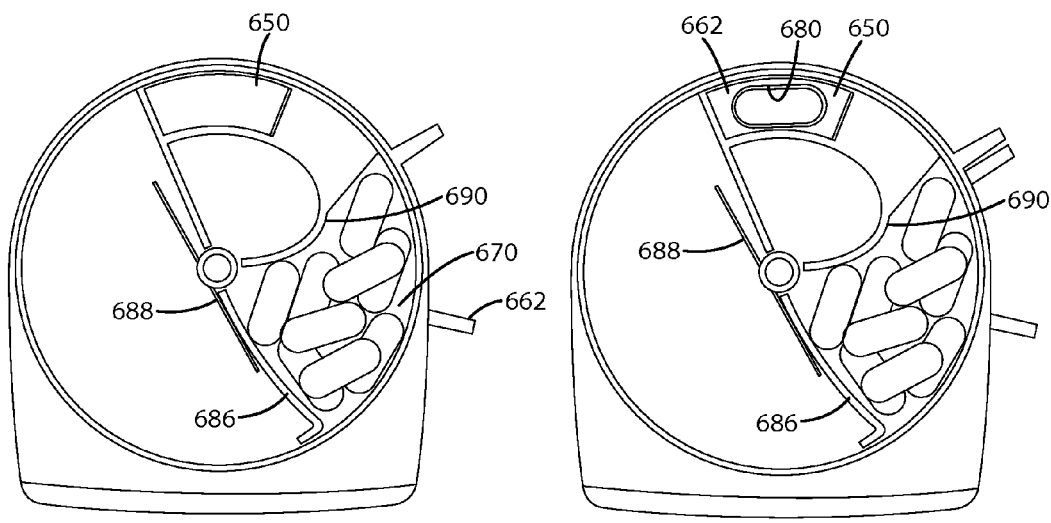
FIG. 38 is a top internal view of the package of FIG. 36.
FIG. 39 is a top internal view of the package of FIG. 36.
Figure 40:
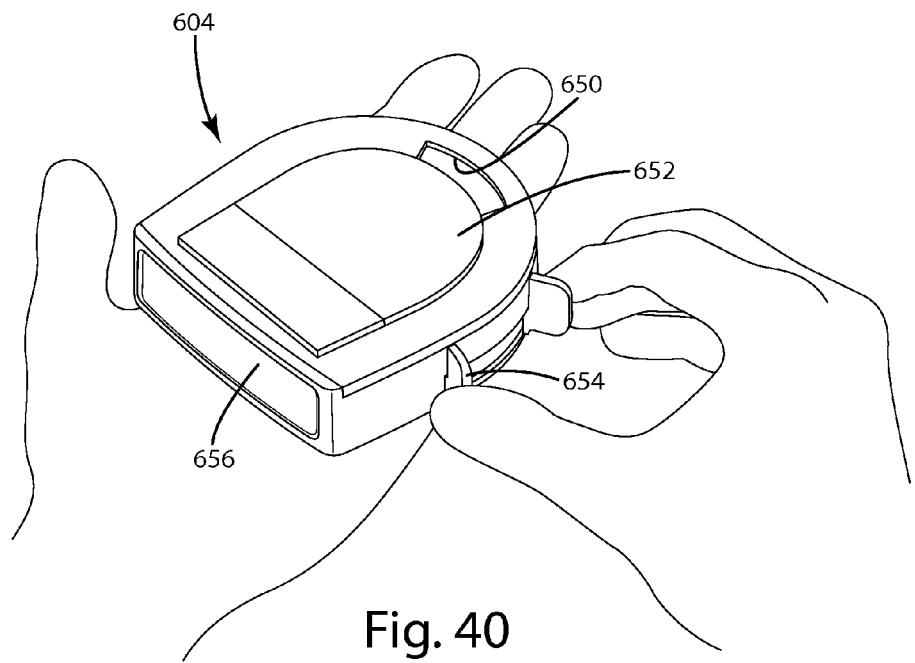
FIG. 40 is a perspective view of the package of FIG. 36 being manually operated to dispense a pill.

The main body 664 of the package 604 is shown in FIG. 37. As seen in FIG. 37, the package 604 includes an internal reservoir 670 for containing loose pills, a pivotal pusher 686 for pushing pills contained in the reservoir 670 and a coil spring 688 for urging the pusher 686 in the proper direction to move pills toward the reservoir outlet (not shown). The reservoir 670 may include a chute 690 for shepherding pills one at a time from the reservoir 670 to the reservoir outlet. Although not shown, the reservoir outlet is an opening disposed at the end of the chute 690 that is shaped to allow a single pill to fall through the floor of the main body 664 to the indexing disc 662. FIGS. 38 and 39 are helpful in understanding operation of the package 604. FIG. 38 shows the indexing disc 662 in the home position. In this position, the pill opening 680 in the indexing disc 662 is aligned with the reservoir outlet in the floor of the main body 664. This allows a pill to fall from the reservoir 670 into the pill opening 680 of the indexing disc 662. The chute 690 and reservoir outlet (not shown) are shaped to properly position each pill to fall into the pill opening 680. FIG. 39 shows the indexing disc 662 in the eject position. In this position, the disc 662 has been rotated to move the pill into the package outlet so that is can fall by gravity from the package 604, for example, to the base 602 and into the tray 612. Although operation of the package 604 has been described in connection with a dispenser system 600 and base 602, it should be recognized that the package 604 may be manually operated separate from the base 602. For example, as shown in FIG. 40, the package 604 may be operated manually to dispense a pill directly into a users hand.

In the illustrated embodiment, the user dispenses the pills manually. In other embodiments, the dispenser system may automate the process of dispensing the appropriate pills at the appropriate time. For example, the dispenser system may operate the packages to dispense the pills at the appropriate time for consumption. The packages may include solenoids, motors or other similar mechanisms capable of actuating the dispensing mechanism at the direction of the dispenser system. In such embodiments, the control system in the base may track dispensing times and send control signals to the appropriate package at the appropriate time to direct the package to actuate the dispenser mechanism to dispense the desired number of pills.

In an alternative embodiment, the dispenser system and/or packages may be provided with security features to help limit unauthorized or inappropriate dispensing of pills. For example, the dispenser system and/or packages can be configured to prevent unprescribed users from taking pills not prescribed to them. In some embodiments, the packages may be made child safe (or child resistant) by requiring operation of more than one mechanism to dispense a pill. For example, in one embodiment, buttons on opposite sides of the package must be pressed simultaneously to dispense a pill. A variety of alternative mechanism can be used to provide this child safe (or child resistant) feature, including any of a variety of known mechanism. If the dispenser system has the ability to automate pill dispensing, the dispenser system may include a security feature that prevents unauthorized dispensing of pills. The dispenser system may continue to provide reminders whether or not the security feature has been deactivated, but the system may be configured not to dispense a pill until the appropriate measures are taken to deactivate the security. For example, the dispenser system may include a password or some form of biometric input required to deactivate the security and authorize the dispenser system to dispense a pill, such as a fingerprint reader or voice recognition/voice identification system. The password may be entered using the touch screen. The fingerprint reader may be incorporated into the base, for example, adjacent to the touch screen. As another example, the dispenser system may have the ability to identify a user based on the presence of an electronic device. The dispenser system may have the ability to key a specific electronic device, such as a cell phone, to a specific user and the dispenser system may require the electronic device to be within proximity of the dispenser system before dispensing pills for that user. The dispenser system may determine the proximity of the keyed electronic devise using capabilities associated with Bluetooth, WiFi, Near Field Communications or other wireless methods and apparatus. For example, during set up, a user may be keyed to a specific smart phone. The dispenser system may be configured to search for the smart phone to be within sufficient proximity before dispensing any pills.

Although the present invention is described in connection with the dispensing of pills to a single individual, the present invention may be configured to provide pills for multiple individuals. In such cases, the reminder may specific the individual that is supposed to take the pill to be dispensed with that reminder. The tracking subsystem may be configured to separately track information for each user. The security features described above can be used to dispense pills only when the appropriate person is within sufficient proximity to the dispenser system. In some applications, the dispenser system may be configured to dispense pills when the appropriate user is the closest individual to the system.

The above description is that of current embodiments of the invention. Various alterations and changes can be made without departing from the spirit and broader aspects of the invention. It is to be understood that the invention disclosed and defined herein extends to all alternative combinations of two or more of the individual features mentioned or evident from the text and/or drawings. All of these different combinations constitute various alternative aspects of the present invention.

The invention claimed is:
1. A pill dispensing system comprising:
a dispenser base;
a plurality of pill packages stackable on the dispenser base to work in conjunction with the dispenser base to dispense pills, each pill package including:
a pill reservoir for storing pills; and
memory for storing pill package information;
an actuatable dispenser for dispensing pills;
said dispenser base that receives the plurality of pill packages, the dispenser base including:
a communication system enabling communication of pill package information including information regarding dispenser actuation from pill packages stacked on the dispenser base to the dispenser base;
a sensor system for detecting pill dispensing, wherein the sensor system includes an IR transmitter and an IR sensor arranged on a through-hole in the dispenser base wherein dispensed pills fall from one of the plurality of pill packages through the through-hole; and
a tracking system for tracking inventory of pills for the plurality of pill packages, wherein information regarding dispenser actuation received from a pill package is coupled with output from the sensor system detecting pill dispensing to determine which pill package dispensed the pill.
2. The pill dispensing system of claim 1 wherein the communication system enables two way communication between the dispenser base and the plurality of pill packages, and wherein the tracking system tracks the inventory of pills for each pill package by querying the plurality of pill packages in response to the sensor system detecting pill dispensing to determine which pill package was actuated.
3. The pill dispensing system of claim 1 wherein the sensor system includes at least one of a weight sensor and an optical sensor.

4. The pill dispensing system of claim 1 wherein the IR transmitter and the IR sensor are arranged on opposite sides of the through-hole in the dispenser base wherein dispensed pills fall from a pill package through the through-hole and fall between the IR transmitter and IR sensor.

5. The pill dispensing system of claim 1 including a reordering system for reordering one or more of the plurality of pill packages in response to the inventory of pills for a pill package falling below a predetermined threshold.

6. The pill dispensing system of claim 1 wherein pill package information includes user information and wherein the tracking system is configured to separately track the inventory of pills for each of a plurality of users.

7. The pill dispensing system of claim 6 wherein the pill dispensing system monitors statistics of when and how often pills are dispensed for each of the plurality of users.

8. The pill dispensing system of claim 6 including a warning system for warning users in response to the inventory of pills of a pill package for that user falling below a predetermined threshold.

9. The pill dispensing system of claim 1 wherein the communication system includes a reader for reading pill package information in response to a pill package being stacked on the dispenser base.

10. The pill dispensing system of claim 1 wherein pill package information includes one or more of: pill type, product quantity, prescribed dosage, manufacturer, manufacturing date, consumer identifier, prescription number, pharmacy contact information, number of refills, refill dates, side effects, and expiration date.

11. The pill dispensing system of claim 1 wherein the communication system enables communicates with a network and is configured to provide information via the network to at least one of a doctor, physician, pharmacist, and food supplement representative.

12. The pill dispensing system of claim 1 wherein pill package information includes user information and the dispenser base includes a control system configured to identify a user based on the presence of an electronic device associated with one of the plurality of users, wherein the control system facilitates operation of the pill dispensing system based on the user information for the identified user.

13. The pill dispensing system of claim 12 wherein presence of the electronic device is determined with at least one of Bluetooth, WiFi, and Near Field Communications.

14. The pill dispensing system of claim 12 wherein the pill package information includes user dosage information, and wherein the control system facilitates operation of the pill dispensing system based on the user dosage information for the identified user.

15. The pill dispensing system of claim 14 wherein the control system is configured to automatically dispense pills from the plurality of pill packages for the identified user based on the user dosage information.

16. The pill dispensing system of claim 14 including a reminder system configured to communicate reminders based on the user dosage information to the identified user via the electronic device associated with that user.

17. The pill dispensing system of claim 1 wherein each of the pill packages is configured to be manually operable to dispense pills without a dispenser base.

18. The pill dispensing system of claim 1 wherein the communication system includes at least one of RFID, Bluetooth, low power RF data transmission, and WiFi.

19. The pill dispensing system of claim 1 wherein the communication system is configured to write information to the memory of the plurality of pill packages.

20. The pill dispensing system of claim 1 wherein the communication system periodically polls the plurality of pill packages.

21. A pill dispensing system comprising:
a dispenser base having a control system to control operation of the pill dispensing system;
a plurality of pill packages stackable on the dispenser base to work in conjunction with the dispenser base to dispense pills, wherein each pill package includes a pill reservoir for storing pills, memory for storing pill package information, and an actuatable dispenser for dispensing pills;
a security system configured to enable authorized dispensing of pills and prevent unauthorized dispensing of pills, the security system including memory for storing predetermined associations between electronic devices and users and predetermined user input for each user; and
wherein the security system authorizes dispensing of pills in response to 1) determining a user is within proximity of the pill dispensing system by detecting presence of an electronic device that was previously associated in memory with that user; and 2) receiving the predetermined user input for that user;
wherein the dispenser base receives the plurality of pill packages and wherein the dispenser base includes:
a communication system enabling communication of pill package information including information regarding dispenser actuation from pill packages stacked on the dispenser base to the dispenser base;
a sensor system for detecting pill dispensing, wherein the sensor system includes an IR transmitter and an IR sensor arranged on a through-hole in the dispenser base wherein dispensed pills fall from one of the plurality of pill packages through the through-hole; and
a tracking system for tracking inventory of pills for the plurality of pill packages, wherein information regarding dispenser actuation received from the plurality of pill packages is coupled with output from the sensor system detecting pill dispensing to determine which pill package dispensed the pill.

22. The pill dispensing system of claim 21 wherein presence of an electronic device is determined with at least one of Bluetooth, WiFi, and Near Field Communications.

23. The pill dispensing system of claim 21 wherein the predetermined user input includes at least one of a password and a biometric input.

24. The pill dispensing system of claim 21 wherein the security system includes a fingerprint reader and the predetermined user input for each user is a fingerprint.

25. The pill dispensing system of claim 21 wherein the security system includes a voice recognition system and the predetermined user input for each user is a voice sample.

26. The pill dispensing system of claim 21 wherein the pill dispensing system includes a communication system configured to receive user dosage information from memory of the plurality of pill packages, wherein the control system is configured to determine an appropriate dispensing schedule based on the user dosage information.

27. The pill dispensing system of claim 21 wherein the control system is configured to search for electronic devices within proximity of the pill dispensing system.

28. The pill dispensing system of claim 21 wherein the communication system enables two way communication between the dispenser base and the plurality of pill packages, and wherein the tracking system tracks the inventory of pills for each pill package by querying the plurality of pill packages in response to the sensor system detecting pill dispensing to determine which pill package was actuated.

29. The pill dispensing system of claim 21 wherein the IR transmitter and the IR sensor are arranged on opposite sides of a through-hole in the dispenser base wherein dispensed pills fall from a pill package through the through-hole and fall between the IR transmitter and IR sensor.

30. The pill dispensing system of claim 21 including a reordering system for reordering one or more of the plurality of pill packages in response to the inventory of pills for a pill package falling below a predetermined threshold.

31. The pill dispensing system of claim 21 wherein pill package information includes user information and wherein the tracking system is configured to separately track the inventory of pills for each of a plurality of users.

32. The pill dispensing system of claim 31 wherein the pill dispensing system monitors statistics of when and how often pills are dispensed for each of the plurality of users.

33. The pill dispensing system of claim 31 including a warning system for warning users in response to the inventory of pills of a pill package for that user falling below a predetermined threshold.

34. The pill dispensing system of claim 21 wherein the pill package information includes user dosage information, and wherein the control system facilitates operation of the pill dispensing system based on the user dosage information for the identified user.

35. The pill dispensing system of claim 34 wherein the control system is configured to automatically dispense pills from the plurality of pill packages for the identified user based on the user dosage information.

36. The pill dispensing system of claim 34 including a reminder system configured to communicate reminders based on the user dosage information to the identified user via the electronic device associated with that user.

37. The pill dispensing system of claim 21 wherein each of the pill packages is configured to be manually operable to dispense pills without a dispenser base.

38. The pill dispensing system of claim 21 wherein the communication system is configured to write information to the memory of the plurality of pill packages.

* * * * *